US007390481B2

(12) United States Patent
Oppmann et al.

(10) Patent No.: US 7,390,481 B2

(45) Date of Patent: Jun. 24, 2008

(54) MAMMALIAN CYTOKINE COMPLEXES

(75) Inventors: Birgit Oppmann, Berlin (DE); Jacqueline C. Timans, Mountain View, CA (US); Robert A. Kastelein, Redwood City, CA (US); J. Fernando Bazan, Menlo Park, CA (US)

(73) Assignee: Schering Corporation, Kenilworth, NJ (US)

( * ) Notice: Subject to any disclaimer, the term of this patent is extended or adjusted under 35 U.S.C. 154(b) by 498 days.

(21) Appl. No.: 10/778,002

(22) Filed: Feb. 11, 2004

(65) Prior Publication Data

US 2004/0192891 A1 Sep. 30, 2004

(51) Int. Cl.

*A61K 38/19* (2006.01)
*A61K 38/22* (2006.01)
*C07K 14/475* (2006.01)
*C07K 14/52* (2006.01)

(52) U.S. Cl. ........................ 424/85.1; 514/12; 530/351; 530/399; 530/402

(58) Field of Classification Search ...................... None
See application file for complete search history.

(56) References Cited

U.S. PATENT DOCUMENTS

| | | | |
|---|---|---|---|
| 5,457,038 | A | 10/1995 | Trinchieri et al. |
| 5,741,772 | A | 4/1998 | Chang |

FOREIGN PATENT DOCUMENTS

| | | | |
|---|---|---|---|
| EP | 0759466 | A2 | 2/1997 |
| WO | WO 95/11303 | A1 | 4/1995 |
| WO | WO 98/11225 | A2 | 3/1998 |
| WO | WO 98/31811 | A1 | 7/1998 |
| WO | WO 98/33922 | A1 | 8/1998 |
| WO | WO 98/49307 | A1 | 11/1998 |
| WO | WO 99/00415 | A1 | 1/1999 |
| WO | WO 99/20755 | A2 | 4/1999 |
| WO | WO 99/28462 | A2 | 6/1999 |
| WO | WO 99/35264 | A1 | 7/1999 |
| WO | WO 99/40195 | A1 | 8/1999 |

OTHER PUBLICATIONS

Rudinger, In "Peptide Hormones" (Ed. J.A. Parsons), University Park Press, Baltimore, pp. 1-7 (1976).*

Peters, et al., "In vivo and in vitro activities of the gp130-stimulating designer cytokine hyper-IL-6," J. Immunol. 161(7):3575-3581 (Oct. 1, 1998).

Rakemann, et al., "the designer cytokine hyper-interleukin-6 is a potent activator of STAT3-dependent gene transcription in vivo and in in vitro," J. Biol. Chem. 274(3):1257-1266 (Jan. 1999).

Senaldi, et al., "Novel neurotrophin-1/B cell-stimulating factor-3: a cytokine of the IL-6 family," Proc. Natl. Acad. Sci. USA 96(20):11458-11463 (Sep. 28, 1999).

Shi, et al. "Computational EST database analysis identifies a novel member of the neuropoletic cytokine family," Biochim. Biophys. Res. Commun., 262(1):132-138 (Aug. 19, 1999).

* cited by examiner

*Primary Examiner*—Robert C. Hayes
(74) *Attorney, Agent, or Firm*—Edwin P. Ching; Sheela Mohan-Peterson

(57) ABSTRACT

Purified genes encoding cytokine from a mammal, reagents related thereto including purified proteins, specific antibodies, and nucleic acids encoding this molecule are provided. Methods of using said reagents and diagnostic kits are also provided.

14 Claims, No Drawings

MAMMALIAN CYTOKINE COMPLEXES

This filing is a conversion to U.S. Utility Patent Application of U.S. Ser. No. 60/124,319, filed Mar. 11, 1999, which is incorporated herein by reference.

FIELD OF THE INVENTION

The present invention pertains to compositions related to proteins which function in controlling biology and physiology of mammalian cells, e.g., cells of a mammalian immune system. In particular, it provides purified genes, proteins, antibodies, related reagents, and methods useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". See, e.g., Paul (1998) *Fundamental Immunology* (4th ed.) Raven Press, NY. Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth factors, e.g., granulocyte colony stimulating factor (G-CSF). See, e.g., Thomson (ed. 1998) *The Cytokine Handbook* (3d ed.) Academic Press, San Diego; Mire-Sluis and Thorpe (ed. 1998) *Cytokines* Academic Press, San Diego; Metcalf and Nicola (1995) *The Hematopoietic Colony Stimulating Factors* Cambridge University Press, and Aggarwal and Gutterman (1991) *Human Cytokines* Blackwell Pub.

Lymphokines apparently mediate cellular activities in a variety of ways. They have been shown to support the proliferation, growth, and/or differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Research to better understand and treat various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

From the foregoing, it is evident that the discovery and development of new lymphokines, e.g., related to G-CSF and/or IL-6, could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. The present invention provides new interleukin compositions and related compounds, and methods for their use.

SUMMARY OF THE INVENTION

The present invention is directed to mammalian, e.g., primate or rodent, interleukin-B60 (IL-B60) and its biological activities. It includes nucleic acids coding for polypeptides themselves and methods for their production and use. The nucleic acids of the invention are characterized, in part, by their homology to complementary DNA (cDNA) sequences disclosed herein, and/or by functional assays for growth factor- or cytokine-like activities, e.g., G-CSF (see Nagata (1994) in Thomson *The Cytokine Handbook* 2d ed., Academic Press, San Diego) and/or IL-6 (see Hirano (1994) in Thomson *The Cytokine Handbook* 2d ed., Academic Press, San Diego). Also provided are polypeptides, antibodies, and methods of using them, including using nucleic acid expression methods. Methods for modulating or intervening in the control of a growth factor dependent physiology or an immune response are provided.

The present invention is based, in part, upon the discovery of a new cytokine sequence exhibiting significant sequence and structural similarity to G-CSF and IL-6. In particular, it provides primate, e.g., human, and rodent, e.g., mouse, genes encoding a protein whose mature size is about 198 amino acids. Functional equivalents exhibiting significant sequence homology will be available from other mammalian, e.g., cow, horse, and rat species.

Moreover, the present invention identifies a second associated component of a complex. Compositions related to the combination of components in the complex are provided, along with methods of use.

In one embodiment, the invention provides a substantially pure or recombinant polypeptide comprising the mature protein portion of SEQ ID NO: 2 or 4. Preferably, the polypeptide is: detectably labeled; unglycosylated; denatured; attached to a solid substrate; conjugated to another chemical moiety; or in a sterile composition. Kit forms include those comprising the polypeptide and: a compartment comprising the polypeptide; or with instructions for use or disposal of reagents in the kit.

Binding compounds include those comprising an antigen binding site from an antibody that specifically binds to the described polypeptide. The binding compound can also be in a kit comprising: a-compartment comprising the binding compound; or with instructions for use or disposal of reagents in the kit.

The invention further provides a method of producing an antigen:antibody complex, comprising contacting, under appropriate conditions, a primate IL-B60 polypeptide with an antibody that specifically or selectively binds the polypeptide of the invention, thereby allowing the complex to form.

Nucleic acid embodiments include an isolated or recombinant polynucleotide encoding the mature protein portion of SEQ ID NO: 2 or 4.

In other embodiments, the invention provides an isolated soluble complex comprising the mature protein portion of SEQ ID NO: 2 or 4, and the mature protein portion of SEQ ID NO: 12 or 13. Preferably the complex: comprises a recombinant polypeptide of SEQ ID NO: 2, 4, 12, or 13; is detectably labeled; is in a buffered solution; is in a sterile solution. Kits are provided containing such a complex and: a compartment comprising the complex; or instructions for use or disposal of reagents in the kit.

Binding compounds are provided comprising an antigen binding site from an antibody that specifically binds to the soluble complex but not to the mature polypeptide of SEQ ID NO: 12 or 13. Kits are provided comprising the binding compound and: a compartment comprising the binding compound; or instructions for use or disposal of reagents in the kit.

Methods are provided, e.g., of producing an antigen:antibody complex, comprising contacting, under appropriate conditions, a primate complex comprising IL-B60 and CLF-1 polypeptides with an antibody that selectively or specifically binds to an isolated soluble complex comprising the mature protein portion of SEQ ID NO: 2 or 4, and the mature protein portion of SEQ ID NO: 12 or 13, thereby allowing the complex to form.

Nucleic acid embodiments include an isolated or recombinant nucleic acid encoding the mature protein portion of SEQ ID NO: 2 or 4, and the mature protein portion of SEQ ID NO: 12 or 13.

The invention also provides a composition of matter selected from: an isolated polypeptide comprising at least seven amino acids identical to segments of SEQ ID NO: 2 or 4; a substantially pure or recombinant polypeptide comprising at least two distinct nonoverlapping segments of at least five amino acids identical to segments of SEQ ID NO: 2 or 4; a natural sequence polypeptide comprising mature SEQ ID NO: 2 or 4; or a fusion polypeptide comprising IL-B60 sequence. In certain embodiments, the distinct nonoverlapping segments of identity include: one of at least eight amino acids; one of at least five amino acids and a second of at least six amino acids; at least three segments of at least four, five, and six amino acids, or one of at least twelve amino acids. In other embodiments the polypeptide of the composition of matter: is the polypeptide which: comprises a mature sequence of Table 1; is an unglycosylated form of IL-B60; is from a primate, such as a human; comprises at least seventeen amino acids of SEQ ID NO: 2 or 4; exhibits at least four nonoverlapping segments of at least seven amino acids of SEQ ID NO: 2 or 4; is a natural allelic variant of IL-B60; has a length at least about 30 amino acids; exhibits at least two non-overlapping epitopes which are specific for a primate IL-B60; is glycosylated; has a molecular weight of at least 30 kD with natural glycosylation; is a synthetic polypeptide; is attached to a solid substrate; is conjugated to another chemical moiety; is a 5-fold or less substitution from natural sequence; is a deletion or insertion variant from a natural sequence; or which further comprises: at least seven amino acids identical to segments of SEQ ID NO: 12 or 13; at least two distinct nonoverlapping segments of at least five amino acids identical to segments of SEQ ID NO: 12 or 13; a natural sequence polypeptide comprising mature SEQ ID NO: 12 or 13; or a primate CLF-1. In additional preferred embodiments, the composition comprises: a substantially pure IL-B60 and CLF-1; a sterile IL-B60 polypeptide comprising the mature protein of SEQ ID NO: 2 or 4; or the described polypeptide and a carrier, wherein the carrier is: an aqueous compound, including water, saline, and/or buffer; and/or formulated for oral, rectal, nasal, topical,mRNA,or parenteral administration. The invention provides fusion polypeptides which comprise: mature protein sequence of Table 1; a detection or purification tag, including a FLAG, His6, or Ig sequence; or sequence of another cytokine receptor family protein, including CLF-1. Kit embodiments include those comprising the polypeptide of the composition and: a compartment comprising the protein or polypeptide; or instructions for use or disposal of reagents in the kit.

The invention further provides methods of using the described polypeptides: to label the polypeptide, comprising labeling the polypeptide with a radioactive label; to separate the polypeptide from another polypeptide in a mixture, comprising running the mixture on a chromatography matrix, thereby separating the polypeptides; to identify a compound that binds selectively to the polypeptide, comprising incubating the compound with the polypeptide under appropriate conditions; thereby causing the component to bind to the polypeptide; or to conjugate the polypeptide to a matrix, comprising derivatizing the polypeptide with a reactive reagent, and conjugating the polypeptide to the matrix.

Related binding compounds include those comprising an antigen binding site from an antibody that specifically or selectively binds to a natural polypeptide, as described above, wherein: the binding compound is in a container; the IL-B60 polypeptide is from a human; the binding compound is an Fv, Fab, or Fab2 fragment; the binding compound is conjugated to another chemical moiety; or the antibody: is raised against a mature polypeptide of Table 1; is raised against a mature IL-B60; is raised to a purified human IL-B60; is immunoselected; is a polyclonal antibody; binds to a denatured IL-B60; exhibits a Kd to antigen of at least 30 μM; is attached to a solid substrate, including a bead or plastic membrane; is in a sterile composition; or is detectably labeled, including a radioactive or fluorescent label. Kits are provided comprising such a binding compound and: a compartment comprising the binding compound; or instructions for use or disposal of the reagents of the kit.

Methods are provided for producing an antigen:antibody complex, comprising contacting, under appropriate conditions, a primate IL-B60 polypeptide with a described antibody, thereby allowing the complex to form. Preferably, in the method: the complex is purified from other cytokines; the complex is purified from other antibody; the contacting is with a sample comprising a cytokine; the contacting allows quantitative detection of the antigen; the contacting is with a sample comprising the antibody; or the contacting allows quantitative detection of the antibody.

In another embodiment the invention includes a composition comprising: a sterile binding compound, as described, or the binding compound and a carrier, wherein the carrier: wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding the described polypeptide, wherein: the IL-B60 is from a human; or the nucleic acid:

encodes an antigenic peptide sequence of Table 1; encodes a plurality of antigenic peptide sequences of Table 1; encodes a plurality of antigenic peptide sequences of Table 4; exhibits identity over at least thirteen nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate; comprises a natural full length coding sequence; is a hybridization probe for a gene encoding the IL-B60; or is a PCR primer, PCR product, or mutagenesis primer. Preferred embodiments include where the isolated or recombinant nucleic acid is in a cell or tissue. The cell may be: a prokaryotic cell; a eukaryotic cell; a bacterial cell; a yeast cell; an insect cell; a mammalian cell; a mouse cell; a primate cell; or a human cell.

Kits are provided comprising the described nucleic acid and: a compartment comprising the nucleic acid; a compartment further comprising a primate IL-B60 polypeptide; or instructions for use or disposal of reagents in the kit.

The invention further provides methods for forming a duplex with a polynucleotide described above, comprising contacting the polynucleotide with a probe that hybridizes, under stringent conditions, to at least 25 contiguous nucleotides of the coding portion of SEQ ID NO: 1, 3, or encoding the nature SEQ ID NO: 12 or 13; thereby forming the duplex.

In a further aspect, the invention provides a nucleic acid which: hybridizes under wash conditions of 30 minutes at 30° C. and less than 2M salt to the coding portion of SEQ ID NO: 1; or exhibits identity over-a stretch of at least about 30 nucleotides to a primate IL-B60. In preferred embodiments, the wash conditions that are at 45° C. and/or 500 mM salt; or at 55° C. and/or 150 mM salt; or the stretch is at least 55 nucleotides, e.g., at least 75 nucleotides.

Methods are provided, e.g., of modulating physiology or development of a cell or tissue culture cells comprising contacting the cell with an agonist or antagonist of a mammalian IL-B60; or contacting the cell with an agonist or antagonist of a complex comprising mammalian IL-B60 and CLF-1. Additionally, the invention provides a method of increasing the secretion of: an IL-B60 sequence, comprising expressing the polypeptide with CLF-1; or a CLF-1, comprising expressing the CLF-1 with an IL-B60 sequence. In preferred embodiments of the method, the increasing is at least 3 fold, 5×, 7×, 10×, or more; or the expressing is of a recombinant nucleic acid encoding one or both of the polypeptide and CLF-1.

The invention further provides a method of screening for a receptor which binds an isolated soluble complex comprising the mature protein portion of SEQ ID NO: 2 or 4, and the mature protein portion of SEQ ID NO: 12 or 13, comprising contacting the complex to a cell expressing the receptor under conditions allowing the complex to bind to the receptor, thereby forming a detectable interaction. Preferably, the interaction results in a physiological response in the cell.

Other embodiments of the invention include, e.g., an isolated soluble complex comprising at least 6 amino acids of the mature protein portion of SEQ ID NO: 2 or 4, and: at least 6 amino acids of the mature protein portion of SEQ ID NO: 12 or 13; or at least 6 amino acids of the mature protein portion of the CNTF-R. Such complex may, e.g., comprise a recombinant polypeptide of mature SEQ ID NO: 2 or 4; comprise a recombinant polypeptide of mature SEQ ID NO: 12 or 13; comprise a recombinant polypeptide of mature CNTF-R; comprise both a recombinant polypeptide of mature SEQ ID NO: 2 or 4, and a recombinant polypeptide of mature SEQ ID NO: 12 or 13; comprise both a recombinant polypeptide of mature SEQ ID NO: 2 or 4, and a recombinant polypeptide of mature CNTF-R; be detectably labeled; be in a buffered solution; or be in a sterile solution. Preferred embodiments include those which: comprise a mature IL-B60 polypeptide; comprise a mature CLF-1 polypeptide; comprises a mature CNTF-R polypeptide; exhibit at least four nonoverlapping segments of at least seven amino acids of SEQ ID NO: 2 or 4; exhibit epitopes from both primate L-B60 and primate CLF-1; exhibit epitopes from both primate L-B60 and primate CNTF-R; not be glycosylated; be attached to a solid substrate; be conjugated to another chemical moiety; or comprise a detection or purification tag, including a FLAG, His6, or Ig sequence.

Kits are provided, e.g., comprising the complex and: a compartment comprising the complex, and/or instructions for use or disposal of reagents in the kit.

Fusion polypeptides are provided, which include, e.g., an isolated or recombinant polypeptide comprising: a first segment comprising at least seven amino acids identical to segments of SEQ ID NO: 2 or 4, and a second segment comprising at least seven amino acids identical to segments of mature SEQ ID NO: 12 or 13; at least two distinct nonoverlapping segments of at least five amino acids identical to segments of mature SEQ ID NO: 2 or 4, and a third segment comprising at least seven amino acids identical to segments of mature SEQ ID NO: 12 or 13; at least one segment comprising at least seven amino acids identical to segments of mature SEQ ID NO: 2 or 4, and two distinct nonoverlapping segments of at least five amino acids identical to segments of mature SEQ ID NO: 12 or 13; a first segment comprising at least seven amino acids identical to segments of SEQ ID NO: 2 or 4, and a second segment comprising at least seven amino acids identical to segments of mature primate CNTF-R; at least two distinct nonoverlapping segments of at least five amino acids identical to segments of mature SEQ ID NO: 2 or 4, and a third segment comprising at least seven amino acids identical to segments of mature primate CNTF-R; or at least one segment comprising at least seven amino acids identical to segments of mature SEQ ID NO: 2 or 4, and two distinct nonoverlapping segments of at least five amino acids identical to segments of mature primate CNTF-R. Certain embodiments include those wherein the distinct nonoverlapping segments of identity: include one of at least eight amino acids; include one of at least five amino acids and a second of at least six amino acids; include at least three segments of at least four, five, and six amino acids, or include one of at least twelve amino acids. Other embodiments include those which: comprise a mature IL-B60 sequence; comprise a mature CLF-1 sequence; comprise a mature CNTF-R sequence; exhibit at least four nonoverlapping segments of at least seven amino acids of SEQ ID NO: 2 or 4; have a length at least about 30 amino acids; exhibit epitopes from both primate IL-B60 and primate CLF-1; exhibits epitopes from both primate IL-B60 and primate CNTF-R; are not glycosylated; have a molecular weight of at least 30 kD; be a synthetic polypeptide; be attached to a solid substrate; be conjugated to another chemical moiety; or comprise a detection or purification tag, including a FLAG, His6, or Ig sequence.

Other embodiments include a composition comprising: substantially pure combination of IL-B60 and CLF-l; substantially pure combination of IL-B60 and CNTF-R; a sterile polypeptide described above; or the polypeptide described above and a carrier, wherein the carrier is: an aqueous compound, including water, saline, and/or buffer; and/or formulated for oral, rectal, nasal, topical, or parenteral administration. A kit is provided comprising a polypeptide as described, and: a compartment comprising the polypeptide; and/or instructions for use or disposal of reagents in the kit.

Methods are also provided, e.g., of making an antibody which recognizes a complex as described, comprising inducing an immune response in an animal with the complex; of immunoselecting antibodies, comprising contacting a population of antibodies to a complex as described, and separating antibodies that bind from those which do not bind; or of formulating a composition, comprising admixing a complex as described with a carrier.

Binding compounds are provided, e.g., comprising an antigen binding site from an antibody, which antibody specifically binds a described complex, but not to any of the mature polypeptides of SEQ ID NO: 2, 4, 12, 13, or CNTF-R. Certain embodiments include those wherein: the binding compound is: in a container; an Fv, Fab, or Fab2 fragment; or conjugated to another chemical moiety; or the antibody: is raised against a substantially pure complex of IL-B60 with CLF-1; is raised against a substantially pure complex of IL-B60 with CNTF-R; is immunoselected; is a polyclonal antibody; exhibits a Kd to antigen of at least 30 μM; is attached to a solid substrate, including a bead or plastic membrane; is in a sterile composition; or is detectably labeled, including a radioactive or fluorescent label. Additional embodiments include a composition comprising: a sterile binding compound as described, or the binding compound as described and a carrier, wherein the carrier is: an aqueous compound, including water, saline, and/or buffer; and/or formulated for oral, rectal, nasal, topical, or parenteral administration.

With the binding composition are provided a kit comprising the binding compound and: a compartment comprising the binding compound; or instructions for use or disposal of reagents in the kit. Also provided are methods of producing an antigen:antibody complex, comprising contacting under appropriate conditions a primate complex comprising: IL-B60 and CLF-1 polypeptides; or IL-B60 and CNTF-R polypeptides; with an antibody as described, thereby allowing the complex to form. Preferably, in the method, the complex is purified from other cytokines; the complex is purified from other antibody; the contacting is with a sample comprising a cytokine; the contacting allows quantitative detection of the antigen; the contacting is with a sample comprising the antibody; or the contacting allows quantitative detection of the antibody.

Various nucleic acids are provided, e.g., an isolated or recombinant nucleic acid: encoding the amino acid portions described above; encoding the amino acid portions as described, and comprise a segment at least 30 contiguous nucleotides from SEQ ID NO: 1 or 3; which will coexpress a segment of at least seven contiguous amino acids from SEQ ID NO: 2 or 4, and a segment of at least seven contiguous amino acids from SEQ ID NO: 12 or 13; or which will coexpress a segment of at least seven contiguous amino acids from SEQ ID NO: 2 or 4, and a segment of at least seven contiguous amino acids from CNTF-R. Preferred nucleic acids include those which, e.g.,: encode IL-B60 from a human; encode CLF-1 from a human; encodes CNTF-R from a human; are an expression vector; further comprise an origin of replication; comprise a detectable label; comprise synthetic nucleotide sequence; or are less than 6 kb, preferably less than 3 kb. A cell comprising the recombinant nucleic acid is provided, e.g., wherein the cell is: a prokaryotic cell; a eukaryotic cell; a bacterial cell; a yeast cell; an insect cell; a mammalian cell; a mouse cell; a primate cell; or a human cell. Various nucleic acid kits are provided, e.g., comprising the nucleic acid and: a compartment comprising the nucleic acid; a compartment further comprising a primate IL-B60 polypeptide; a compartment further comprising a primate CLF-1 polypeptide; a compartment further comprising a primate CNTF-R polypeptide; or instructions for use or disposal of reagents in the kit. Methods are also provided, e.g., of making a duplex nucleic acid, comprising contacting such a nucleic acid with a complementary nucleic acid under appropriate conditions, thereby forming said duplex; of expressing a polypeptide, comprising expressing the nucleic acid, thereby producing the polypeptide; or of transfecting a cell, comprising contacting said cell under appropriate conditions with the nucleic acid, thereby transfecting the cell.

In an alternative embodiment, the invention provides an isolated or recombinant nucleic acid which encodes at least 5 contiguous amino acids of SEQ ID NO: 12, 13, or primate CNTF-R and: hybridizes under wash conditions of 30 minutes at 30° C. and less than 2M salt to the coding portion of SEQ ID NO: 1; or exhibits identity over a stretch of at least about 30 nucleotides to a primate IL-B60. Preferred embodiments include: the isolated nucleic acid, wherein: the contiguous amino acids number at least 8; the wash conditions are at 45° C. and/or 500 mM salt; or the stretch is at least 55 nucleotides; or the recombinant nucleic acid, wherein: the contiguous amino acids number at least 12; the wash conditions are at 55° C. and/or 150 mM salt; or the stretch is at least 75 nucleotides.

The invention particularly provides methods of modulating physiology or development of a cell or tissue culture cells comprising contacting the cell with an agonist or antagonist of a complex comprising mammalian IL-B60 and: CLF-1; or CNTF-R. It also provides methods of producing the proteins, e.g., producing a complex described, comprising coexpressing a recombinant IL-B60 with a recombinant CLF-1 or CNTF-R; increasing the secretion of an IL-B60 polypeptide comprising expressing the polypeptide with CLF-1 or CNTF-R; or increasing the secretion of a CLF-1 polypeptide, comprising expressing the CLF-1 with an IL-B60. Typically, the increasing is at least 3 fold; or the expressing is of a recombinant nucleic acid encoding one or both of the polypeptide and CLF-1.

Also provided are methods of screening for a receptor which binds the described complex, comprising contacting the complex to a cell expressing the receptor under conditions allowing the complex to bind to the receptor, thereby forming a detectable interaction. Preferably, the interaction results in a physiological response in the cell.

DETAILED DESCRIPTION OF THE PREFERRED EMBODIMENTS

All references cited herein are incorporated herein by reference to the same extent as if each individual publication or patent application was specifically and individually indicated to be incorporated by reference.

Outline

I. General
II. Purified IL-B60 or complex
  A. physical properties
  B. biological properties
III. Physical Variants
  A. sequence variants, fragments
  B. post-translational variants
    1. glycosylation
    2. others
IV. Functional Variants
  A. analogs, fragments
    1. agonists
    2. antagonists -continued B. mimetics
  1. protein
  2. chemicals
C. species variants
V. Antibodies
A. polyclonal
B. monoclonal
C. fragments, binding compositions
VI. Nucleic Acids
A. natural isolates; methods
B. synthetic genes
C. methods to isolate
VII. Making IL-B60 or complex, mimetics
A. recombinant methods
B. synthetic methods
C. natural purification
VIII. Uses
A. diagnostic
B. therapeutic
IX. Kits
A. nucleic acid reagents
B. protein reagents
C. antibody reagents
X. Isolating receptors for IL-B60 or complex I. General The present invention provides amino acid sequences and DNA sequences encoding various mammalian proteins which are cytokines, e.g., which are secreted molecules which can mediate a signal between immune or other cells. See, e.g., Paul (1998) *Fundamental Immunology* (4th ed.) Raven Press, N.Y. The full length cytokines, and fragments, or antagonists will be useful, e.g., in physiological modulation of cells expressing a receptor. It is likely that IL-B60 has either stimulatory or inhibitory effects on hematopoietic cells, including, e.g., lymphoid cells, such as T-cells, B-cells, natural killer (NK) cells, macrophages, dendritic cells, hematopoietic progenitors, etc. The proteins will also be useful as antigens, e.g., immunogens, for raising antibodies to various epitopes on the protein, both linear and conformational epitopes.

A sequence encoding IL-B60 was identified from a human genomic sequence. The molecule was designated huIL-B60. A rodent sequence, e.g., from mouse, is also described.

The human gene encodes a small soluble cytokine-like protein, of about 198 amino acids. The psort predicted signal sequence probably is about 17 residues, and would run from the Met to about Ala. See Table 1 and SEQ. ID. NO: 1 and 2. IL-B60 exhibits structural motifs characteristic of a member of the long chain cytokines. Compare, e.g., IL-B60, G-CSF, and IL-6, sequences available from GenBank. Closest matching is with CT-1, oncostatin M, and CNTF. See also Table 2.

TABLE 1

Nucleic acid (SEQ ID NO: 1) encoding IL-B60 from a primate, e.g., human. Predicted signal cleavage site is indicated. Nucleotide 375 may be A. Translated amino acid sequence is SEQ ID NO: 2.

```
ccgagcgaaa aaaacctgcg agtgggcctg gcggatggga ttattaaagc ttcgccggag    60

ccgcggctcg ccctcccact ccgccagcct ccgggagagg agccgcaccc ggccggcccg   120

gccccagccc catggacctc cgagcagggg actcgtgggg g atg tta gcg tgc ctg   176
                                              Met Leu Ala Cys Leu
                                                          -15

tgc acg gtg ctc tgg cac ctc cct gca gtg cca gct ctc aat cgc aca     224
Cys Thr Val Leu Trp His Leu Pro Ala Val Pro Ala Leu Asn Arg Thr
        -10                 -5                  -1   1

ggg gac cca ggg cct ggc ccc tcc atc cag aaa acc tat gac ctc acc     272
Gly Asp Pro Gly Pro Gly Pro Ser Ile Gln Lys Thr Tyr Asp Leu Thr
  5                  10                  15                  20

cgc tac ctg gag cac caa ctc cgc agc ttg gct ggg acc tat ctg aac     320
Arg Tyr Leu Glu His Gln Leu Arg Ser Leu Ala Gly Thr Tyr Leu Asn
                 25                  30                  35

tac ctg ggc ccc cct ttc aac gag cca gac ttc aac cct ccc cgc ctg     368
Tyr Leu Gly Pro Pro Phe Asn Glu Pro Asp Phe Asn Pro Pro Arg Leu
             40                  45                  50

ggg gca gag act ctg ccc agg gcc act gtt gac ttg gag gtg tgg cga     416
Gly Ala Glu Thr Leu Pro Arg Ala Thr Val Asp Leu Glu Val Trp Arg
         55                  60                  65

agc ctc aat gac aaa ctg cgg ctg acc cag aac tac gag gcc tac agc     464
Ser Leu Asn Asp Lys Leu Arg Leu Thr Gln Asn Tyr Glu Ala Tyr Ser
     70                  75                  80

cac ctt ctg tgt tac ttg cgt ggc ctc aac cgt cag gct gcc act gct     512
His Leu Leu Cys Tyr Leu Arg Gly Leu Asn Arg Gln Ala Ala Thr Ala
 85                  90                  95                 100

gag ctg cgc cgc agc ctg gcc cac ttc tgc acc agc ctc cag ggc ctg     560
Glu Leu Arg Arg Ser Leu Ala His Phe Cys Thr Ser Leu Gln Gly Leu
                105                 110                 115
```

TABLE 1-continued

Nucleic acid (SEQ ID NO: 1) encoding IL-B60 from a primate, e.g., human. Predicted signal cleavage site is indicated. Nucleotide 375 may be A. Translated amino acid sequence is SEQ ID NO: 2.

| | |
|---|---|
| ctg ggc agc att gcg ggc gtc atg gca gct ctg ggc tac cca ctg ccc | 608 |
| Leu Gly Ser Ile Ala Gly Val Met Ala Ala Leu Gly Tyr Pro Leu Pro | |
| 120 125 130 | |
| cag ccg ctg cct ggg act gaa ccc act tgg act cct ggc cct gcc cac | 656 |
| Gln Pro Leu Pro Gly Thr Glu Pro Thr Trp Thr Pro Gly Pro Ala His | |
| 135 140 145 | |
| agt gac ttc ctc cag aag atg gac gac ttc tgg ctg ctg aag gag ctg | 704 |
| Ser Asp Phe Leu Gln Lys Met Asp Asp Phe Trp Leu Leu Lys Glu Leu | |
| 150 155 160 | |
| cag acc tgg ctg tgg cgc tcg gcc aag gac ttc aac cgg ctc aag aag | 752 |
| Gln Thr Trp Leu Trp Arg Ser Ala Lys Asp Phe Asn Arg Leu Lys Lys | |
| 165 170 175 180 | |
| aag atg cag cct cca gca gct gca gtc acc ctg cac ctg ggg gct cat | 800 |
| Lys Met Gln Pro Pro Ala Ala Ala Val Thr Leu His Leu Gly Ala His | |
| 185 190 195 | |
| ggc ttc tgacttctga ccttctcctc ttcgctcccc cttcaaaccc tgctcccact | 856 |
| Gly Phe | |
| ttgtgagagc cagccctgta tgccaacacc tgttgagcca ggagacagaa gctgtgagcc | 916 |
| tctggccctt tcctggaccg gctgggcgtg tgatgcgatc agccctgtct cctccccacc | 976 |
| tcccaaaggt ctaccgagct ggggaggagg tacagtaggc cctgtcctgt cctgtttcta | 1036 |
| caggaagtca tgctcgaggg agtgtgaagt ggttcaggtt ggtgcagagg cgctcatggc | 1096 |
| ctcctgcttc ttgcctacca cttggccagt gcccacccag cccctcaggt ggcacatctg | 1156 |
| gagggcaggg gttgaggggc caccaccaca catgcctttc tggggtgaag ccctttggct | 1216 |
| gccccactct ccttggatgg gtgttgctcc cttatcccca aatcactcta tacatccaat | 1276 |
| tcaggaaaca aacatggtgg caattctaca caaaaagaga tgagattaac agtgcagggt | 1336 |
| tggggtctgc attggaggtg ccctataaac cagaagagaa aatactgaaa gcacaggggc | 1396 |
| agggacagac cagaccagac ccaggagtct ccaaagcaca gagtggcaaa caaaacccga | 1456 |
| gctgagcatc aggaccttgc ctcgaattgt cttccagtat tacggtgcct cttctctgcc | 1516 |
| ccctttccca gggtatctgt gggttgccag gctggggagg gcaaccatag ccacaccaca | 1576 |
| ggatttcctg aaagtttaca atgcagtagc attttggggt gtagggtggc agctccccaa | 1636 |
| ggccctgccc cccagcccca cccactcatg actctaagtg tgttgtatta atatttattt | 1696 |
| atttggagat gttatttatt agatgatatt tattgcagaa tttctattct tgtattaaca | 1756 |
| aataaaatgc ttgccccaga acaaaaaaaa aaaa | 1790 |

MLACLCTVLWHLPAVPA/LNRTGDPGPGPSIQKTYDLTRYLEHQLRSLAGTYLNYLGPPFNEPDFNPPR

LGAETLPRATVDLEVWRSLNDKLRLTQNYEAYSHLLCYLRGLNRQAATAELRRSLAHFCTSLQGLLGSI

AGVMAALGYPLPQPLPGTEPTWTPGPAHSDFLQKMDDFWLLKELQTWLWRSAKDFNRLKKKMQPPAAAV

TLHLGAHGF

Rodent, e.g., mouse, IL-B60 (SEQ ID NO: 3 and 4):

| | |
|---|---|
| atg tta gct tgc cta tgc acg gtg ctg tgg cac ctc cct gca gtg cca | 48 |
| Met Leu Ala Cys Leu Cys Thr Val Leu Trp His Leu Pro Ala Val Pro | |
| -15 -10 -5 | |
| gct ctt aat cgc aca gga gat cca ggc cct ggc ccc tcc atc cag aaa | 96 |
| Ala Leu Asn Arg Thr Gly Asp Pro Gly Pro Gly Pro Ser Ile Gln Lys | |
| -1 1 5 10 15 | |
| acc tat gac ctc acc cgc tac ctg gag cat caa ctc cgc agc tta gct | 144 |
| Thr Tyr Asp Leu Thr Arg Tyr Leu Glu His Gln Leu Arg Ser Leu Ala | |
| 20 25 30 | |

TABLE 1-continued

Nucleic acid (SEQ ID NO: 1) encoding IL-B60 from a primate, e.g., human. Predicted signal cleavage site is indicated. Nucleotide 375 may be A. Translated amino acid sequence is SEQ ID NO: 2.

```
ggg acc tac ctg aac tac ctg ggg ccc cct ttc aac gag cct gac ttc    192
Gly Thr Tyr Leu Asn Tyr Leu Gly Pro Pro Phe Asn Glu Pro Asp Phe
             35                  40                  45

aat cct cct cga ctg ggg gca gaa act ctg ccc agg gcc acg gtc aac    240
Asn Pro Pro Arg Leu Gly Ala Glu Thr Leu Pro Arg Ala Thr Val Asn
         50                  55                  60

ttg gaa gtg tgg cga agc ctc aat gac agg ctg cgg ctg acc cag aac    288
Leu Glu Val Trp Arg Ser Leu Asn Asp Arg Leu Arg Leu Thr Gln Asn
     65                  70                  75

tat gag gcg tac agt cac ctc ctg tgt tac ttg cgt ggc ctc aac cgt    336
Tyr Glu Ala Tyr Ser His Leu Leu Cys Tyr Leu Arg Gly Leu Asn Arg
 80                  85                  90                  95

cag gct gcc aca gct gaa ctc cga cgt agc ctg gcc cac ttc tgt acc    384
Gln Ala Ala Thr Ala Glu Leu Arg Arg Ser Leu Ala His Phe Cys Thr
                100                 105                 110

agc ctc cag ggc ctg ctg ggc agc att gca ggt gtc atg gcg acg ctt    432
Ser Leu Gln Gly Leu Leu Gly Ser Ile Ala Gly Val Met Ala Thr Leu
            115                 120                 125

ggc tac cca ctg ccc cag cct ctg cca ggg act gag cca gcc tgg gcc    480
Gly Tyr Pro Leu Pro Gln Pro Leu Pro Gly Thr Glu Pro Ala Trp Ala
        130                 135                 140

cct ggc cct gcc cac agt gac ttc ctc cag aag atg gat gac ttc tgg    528
Pro Gly Pro Ala His Ser Asp Phe Leu Gln Lys Met Asp Asp Phe Trp
    145                 150                 155

ctg ctg aag gag ctg cag acc tgg cta tgg cgt tca gcc aag gac ttc    576
Leu Leu Lys Glu Leu Gln Thr Trp Leu Trp Arg Ser Ala Lys Asp Phe
160                 165                 170                 175

aac cgg ctt aag aag aag atg cag cct cca gca gct tca gtc acc ctg    624
Asn Arg Leu Lys Lys Lys Met Gln Pro Pro Ala Ala Ser Val Thr Leu
                180                 185                 190

cac ttg gag gcc cat ggt ttc tga                                    648
His Leu Glu Ala His Gly Phe
            195

MLACLCTVLWHLPAVPA/LNRTGDPGPGPSIQKTYDLTRYLEHQLRSLAGTYLNYLGPPFNEPDFNPPR

LGAETLPRATVNLEVWRSLNDRLRLTQNYEAYSHLLCYLRGLNRQAATAELRRSLAHFCTSLQGLLGSI

AGVMATLGYPLPQPLPGTEPAWAPGPAHSDFLQKMDDFWLLKELQTWLWRSAKDFNRLKKKMQPPAASV

TLHLEAHGF
```

TABLE 2

Comparison of primate and rodent embodiments of IL-B60, both the nucleotide and amino acid sequences.

```
hIL-B60 ATGTTAGCGTGCCTGTGCACGGTGCTCTGGCACCTCCCTGCAGTGCCAGCTCTCAATCGC
mIL-B60 ATGTTAGCTTGCCTATGCACGGTGCTGTGGCACCTCCCTGCAGTGCCAGCTCTTAATCGC
        ******** ***** *********** ************************** ******

hIL-B60 ACAGGGGACCCAGGGCCTGGCCCCTCCATCCAGAAAACCTATGACCTCACCCGCTACCTG
mIL-B60 ACAGGAGATCCAGGCCCTGGCCCCTCCATCCAGAAAACCTATGACCTCACCCGCTACCTG
        ***** ** ***** *********************************************

hIL-B60 GAGCACCAACTCCGCAGCTTGGCTGGGACCTATCTGAACTACCTGGGCCCCCTTTCAAC
mIL-B60 GAGCATCAACTCCGCAGCTTAGCTGGGACCTACCTGAACTACCTGGGGCCCCCTTTCAAC
        ***** ************** *********** ************** ************

hIL-B60 GAGCCAGACTTCAACCCTCCCCGCCTGGGGGCAGAGACTCTGCCCAGGGCCACTGTTGAC
mIL-B60 GAGCCTGACTTCAATCCTCCTCGACTGGGGGCAGAAACTCTGCCCAGGGCCACGGTCAAC
        ***** ******** ***** ** *********** ***************** **  **
```

TABLE 2-continued

Comparison of primate and rodent embodiments of IL-B60, both the nucleotide and amino acid sequences.

```
hIL-B60  TTGGAGGTGTGGCGAAGCCTCAATGACAAACTGCGGCTGACCCAGAACTACGAGGCCTAC
mIL-B60  TTGGAAGTGTGGCGAAGCCTCAATGACAGGCTGCGGCTGACCCAGAACTATGAGGCGTAC
         ***** **********************  ******************** ***** ***

hIL-B60  AGCCACCTTCTGTGTTACTTGCGTGGCCTCAACCGTCAGGCTGCCACTGCTGAGCTGCGC
mIL-B60  AGTCACCTCCTGTGTTACTTGCGTGGCCTCAACCGTCAGGCTGCCACAGCTGAACTCCGA
         ** ***** ************************************** ***** ** **

hIL-B60  CGCAGCCTGGCCCACTTCTGCACCAGCCTCCAGGGCCTGCTGGGCAGCATTGCGGGCGTC
mIL-B60  CGTAGCCTGGCCCACTTCTGTACCAGCCTCCAGGGCCTGCTGGGCAGCATTGCAGGTGTC
         ** ***************** ******************************** ** ***

hIL-B60  ATGGCAGCTCTGGGCTACCCACTGCCCCAGCCGCTGCCTGGGACTGAACCCACTTGGACT
mIL-B60  ATGGCGACGCTTGGCTACCCACTGCCCCAGCCTCTGCCAGGGACTGAGCCAGCCTGGGCC
         *****  * ** ******************** ***** ******** **  * *** *

hIL-B60  CCTGGCCCTGCCCACAGTGACTTCCTCCAGAAGATGGACGACTTCTGGCTGCTGAAGGAG
mIL-B60  CCTGGCCCTGCCCACAGTGACTTCCTCCAGAAGATGGATGACTTCTGGCTGCTGAAGGAG
         ************************************** *********************

hIL-B60  CTGCAGACCTGGCTGTGGCGCTCGGCCAAGGACTTCAACCGGCTCAAGAAGAAGATGCAG
mIL-B60  CTGCAGACCTGGCTATGGCGTTCAGCCAAGGACTTCAACCGGCTTAAGAAGAAGATGCAG
         ************** ***** ** ******************** ***************

hIL-B60  CCTCCAGCAGCTGCAGTCACCCTGCACCTGGGGGCTCATGGCTTCTGA
mIL-B60  CCTCCAGCAGCTTCAGTCACCCTGCACTTGGAGGCCCATGGTTTCTGA
         ************ ************** *** *** ***** ******
```

Alignment of IL-B60: underlined are proposed helices. In general, those residues that are in helix A and D and not pointing inward toward the core (mostly the hydrophobic residues in A and D helix) are the most likely residues to interact with receptors.

```
                                                A
hIL-B60  MLACLCTVLWHLPAVPALNRTGDPGPGPSIQKTYDLTRYLEHQLRSLAGT
mIL-B60  MLACLCTVLWHLPAVPALNRTGDPGPGPSIQKTYDLTRYLEHQLRSLAGT
         **************************************************

                                                      B
hIL-B60  YLNYLGPPFNEPDFNPPRLGAETLPRATVDLEVWRSLNDKLRLTQNYEAY
mIL-B60  YLNYLGPPFNEPDFNPPRLGAETLPRATVNLEVWRSLNDRLRLTQNYEAY
         *****************************:*********:**********

                                                C
hIL-B60  SHLLCYLRGLNRQAATAELRRSLAHFCTSLQGLLGSIAGVMAALGYPLPQ
mIL-B60  SHLLCYLRGLNRQAATAELRRSLAHFCTSLQGLLGSIAGVMATLGYPLPQ
         ******************************************:*******

                                                D
hIL-B60  PLPGTEPTWTPGPAHSDFLQKMDDFWLLKELQTWLWRSAKDFNRLKKKMQ
mIL-B60  PLPGTEPAWAPGPAHSDFLQKMDDFWLLKELQTWLWRSAKDFNRLKKKMQ
         *******:*:****************************************

hIL-B60  PPAAAVTLHLGAHGF
mIL-B60  PPAASVTLHLEAHGF
         ****:***** ****
```

TABLE 3

Comparison of various cytokines compared to IL-B60. Human IL-B60 is SEQ ID NO: 2; mouse IL-B60 is SEQ ID NO: 4; mouse LIF (mLIF) is SEQ ID NO: 5 and Accession number X06381; human LIF (hLIF) is SEQ ID NO: 6 and Accession numbers M63420 J05436; human CT-1 (hCT-1) is SEQ ID NO: 7 and Accession number U43030; mouse CT-1 (mCT-1) is SEQ ID NO: 8 and Accession number U18366; human CNTF (hCNTF) is SEQ ID NO: 9 and Accession number X60542; mouse CNTF (mCNTF) is SEQ ID NO: 10 and Accession number U05342; human DNAX IL-40 (hDIL-40) is SEQ ID NO: 11.

```
mLIF      -MKVLAAGIVPLLLLVLHWKHGAGSPLPI-TPVNATC-AIRHPCHGNLMN
hLIF      -MKVLAAGVVP-LLLVLHWKHGAGSPLPI-TPVNATC-AIRHPCHNNLMN
hCT-1     --MSRREGSLE---D--PQTDSSVSLLPH-LEA-----KIRQT-HS--LA
```

TABLE 3-continued

Comparison of various cytokines compared to IL-B60. Human IL-B60 is SEQ ID NO: 2; mouse IL-B60 is SEQ ID NO: 4; mouse LIF (mLIF) is SEQ ID NO: 5 and Accession number X06381; human LIF (hLIF) is SEQ ID NO: 6 and Accession numbers M63420 J05436; human CT-1 (hCT-1) is SEQ ID NO: 7 and Accession number U43030; mouse CT-1 (mCT-1) is SEQ ID NO: 8 and Accession number U18366; human CNTF (hCNTF) is SEQ ID NO: 9 and Accession number X60542; mouse CNTF (mCNTF) is SEQ ID NO: 10 and Accession number U05342; human DNAX IL-40 (hDIL-40) is SEQ ID NO: 11.

```
mCT-1     --MSQREGSLE---D--HQTDSSISFLPH-LEA-----KIRQT-HN--LA
hIL-B60   -MLACLCTVLW------HLPAVPALNRTG-DPG-PGP-SIQKT-YD--LT
mIL-B60   -MLACLCTVLW------HLPAVPALNRTG-DPG-PGP-SIQKT-YD--LT
hCNTF     ------MAFTE------HSPLTPHR-R---D-L-CSR-SIW-------LA
mCNTF     ------MAFAE------QSPLTLHR-R---D-L-CSR-SIW-------LA
hDIL-40   MTHLSLLGPLPCVRTSQQLPETQQVTTPGKKPVSVGRREVRVP-----GT
                                                 :     .

mLIF      QIKNQLAQLNQSANALFISYYTAQGEPF--PNNVEK-LCAPNMTDFPSFH
hLIF      QIRSQLAQLNGSANALFILYYTAQGEPF--PNNLDK-LCGPNVTDFPPFH
hCT-1     HLLTKYAEQ------LLQEYVQLQGDPFGLPSFSPPRLPVAGLSAPAPSH
mCT-1     RLLTKYAEQ------LLEEYVQQQGEPFGLPGFSPPRLPLAGLSGPAPSH
hIL-B60   RYLEHQLRS------LAGTYLNYLGPPFNEPDFNPPRLGAETLPRATVDL
mIL-B60   RYLEHQLRS------LAGTYLNYLGPPFNEPDFNPPRLGAETLPRATVNL
hCNTF     RKIRSDLTA------LTESYVKHQG--LNK---NINLDSADGMPVASTD-
mCNTF     RKIRSDLTA------LMESYVKHQG--LNK---NISLDSVDGVPVASTD-
hDIL-40   ALVPSLLSV------SVLLQLQYQGSPFSDPGFSAPELQLSSLPPATAFF
                                  *  :.  .          :.  .

mLIF      ---GNGTEKTKLVELYRMVAYLSASLTNITR-DQKVLNPTAVSLQVKLNA
hLIF      ---ANGTEKAKLVELYRIVVYLGTSLGNITR-DQKILNPSALSLHSKLNA
hCT-1     ---AGLPVHERLRLDAAALAALPPLLDAVCR-RQAELNPRAPRLLRRLED
mCT-1     ---AGLPVSERLRQDAAALSVLPALLDAVRR-RQAELNPRAPRLLRSLED
hIL-B60   EVWRSLNDKLRLTQNYEAYSHLLCYLRGLN--RQAATAELRRSLAHFCTS
mIL-B60   EVWRSLNDRLRLTQNYEAYSHLLCYLRGLN--RQAATAELRRSLAHFCTS
hCNTF     -QWSELTEAERLQENLQAYRTFHVLLARLLEDQQVHFTPTEGDFHQAIHT
mCNTF     -RWSEMTEAERLQENLQAYRTFQGMLTKLLEDQRVHFTPTEGDFHQAIHT
hDIL-40   KTWHALDDGERLSLAQRAID---PHLQLVED-DQSDLNPGSPILPAQLGA
          :         :*             *  :    :         :

mLIF      TIDVMRGLLSNVLCRLCNKYRV--GHVDVPP-----VPDHSDKE--AFQR
hLIF      TADILRGLLSNVLCRLCSKYHV--GHVDVTY-----GPDTSGKD--VFQK
hCT-1     AARQARALGAAVEALLAALGAANRGPRAEPP--AATASAASATG--VFPA
mCT-1     AARQVRALGAAVETVLAALGAAARGPGPEPVTVATLFTANSTAG--IFSA
hIL-B60   LQGLLGSIAGVMAALGYPLPQP--LPGTEPT----WTPGPAHS---DFLQ
mIL-B60   LQGLLGSIAGVMATLGYPLPQP--LPGTEPA----WAPGPAHS---DFLQ
hCNTF     LLLQVAAFAYQIEELMILLEYK--IPRNEAD----GMPINVGDGG-LFEK
mCNTF     LTLQVSAFAYQLEELMALLEQK--VPEKEAD----GMPVTIGDGG-LFEK
hDIL-40   ARLRAQGPLGNMAAIMTALGLP--IP-PEED-----TPGLAAFGASAFER
                .    :                         .         *

mLIF      KKLGCQLLGTYKQVIS----VVVQAF---------------------
hLIF      KKLGCQLLGKYKQIIA----VLAQAF---------------------
hCT-1     KVLGLRVCGLYREWLSRTEGDLGQLLPGGSA----------------
mCT-1     KVLGFHVCGLYGEWVSRTEGDLGQLVPGGVA----------------
hIL-B60   KMDDFWLLKELQTWLWRSAKDFNRLKKKMQPPAAAVTLHLGAHGF--
mIL-B60   KMDDFWLLKELQTWLWRSAKDFNRLKKKMQPPAASVTLHLEAHGF--
hCNTF     KLWGLKVLQELSQWTVRSIHDL-RFISSHQTGIPARGSHYIANNKKM
mCNTF     KLWGLKVLQELSQWTVRSIHDL-RVISSHHMGISAHESHYGA--KQM
hDIL-40   KCRGYVVTREYGHWTDRAVRDLALLKAKYSA----------------
          *  .  :        .     .                :   :.
```

The structural homology of IL-B60 to related cytokine proteins suggests related function of this molecule. IL-B60 is a long chain cytokine exhibiting sequence similarity to IL-6 and G-CSF.

IL-B60 agonists, or antagonists, may also act as functional or receptor antagonists, e.g., which block IL-6 or G-CSF binding to their respective receptors, or mediating the opposite actions. Thus, IL-B60, or its antagonists, may be useful in the treatment of abnormal medical conditions, including immune disorders, e.g., T cell immune deficiencies, chronic inflammation, or tissue rejection, or in cardiovascular or neurophysiological conditions.

The natural antigens are capable of mediating various biochemical responses which lead to biological or physiological responses in target cells. The preferred embodiment characterized herein is from human, but other primate, or other species counterparts exist in nature. Additional sequences for proteins in other mammalian species, e.g., primates, canines, felines, and rodents, should also be available. See below. The descriptions below are directed, for exemplary purposes, to a human IL-B60, but are likewise applicable to related embodiments from other species.

In particular, the association of the IL-B60 with a partner has been confirmed. The IL-B60 and CLF-1 molecules have likely evolved together, reflected in their homology between species. For example, the coevolution of their function is suggested by the observation that the human/mouse relationship of the IL-B60 is very close, as is the human/mouse CLF-1. If the two functionally associate, they might act together in the fashion of IL-12. See, e.g., Trinchieri (1998) *Adv. Immunol.* 70:83-243; Gately, et al.(1998) *Ann. Rev. Immunol.* 16:495-521; and Trinchieri (1998) *Int. Rev. Immunol.* 16:365-396.

As a complex, however, they will interact with two tall receptors in the cytokine receptor family, e.g., gp130, LIF-R, OSM-R, IL-12Rb1, IL-12Rb2, and NR30. These receptors will be tested for binding to the soluble complex. A series of BAF/3 cells that stably express various of these tall receptors have been constructed.

The supernatants of transfectants of both IL-B60 and CLF-1 (or a single combination construct) in the same cell, will be used to test these various BAF/3 cells to see if there is a proliferative or other signaling response. As such, most of the physiological effects of the cytokine may be due to the complex of the proteins. As such, many of the descriptions below of biology resulting from the cytokine may actually be physiologically effected by the complex comprising the combination of the subunits.

Table 4 provides the sequences of the IL-B60 partner, known as CLF-1. The CNTF receptor (CNTF-R) subunit alpha was described, e.g., by Davis, et al. (1991) Science 253:59-63. See also GenBank accession numbers NM1001842 and M73238 (human); AF068615 (mouse); and S54212 (rat); each of which is incorporated herein by reference.

TABLE 4

Alignment of human and mouse Cytokine-Like Factor 1 (CLF-1; SEQ ID NO: 12 and 13) See Elson, et al. (1998) J. Immunol. 161:1371-1379; GenBank Accession number AF059293 and NM_004750; also described by Douglas J. Hilton (Australia) in WO9920755. Reported signal sequence of 37 amino acids in human form, cleavage at GSG/AHT.

```
hCLF-1   MPAGRRGPAAQSARRPPPLLPLLLLLCVLGAPRAGSGAHTAVISPQDPTL
mCLF-1   --------------RPLSSLWSPLLLCVLGVPRGGSGAHTAVISPQDPTL
                       ** . *   *******.**.****************

hCLF-1   LIGSSLLATCSVHGDPPGATAEGLYWTLNGRRLPPELSRVLNASTLALAL
mCLF-1   LIGSSLQATCSIHGDTPGATAEGLYWTLNGRRLP-SLSRLLNTSTLALAL
         ****** ****:***.****************** .***:**:*******

hCLF-1   ANLNGSRQRSGDNLVCHARDGSILAGSCLYVGLPPEKPVNISCWSKNMKD
mCLF-1   ANLNGSRQQSGDNLVCHARDGSILAGSCLYVGLPPEKPFNISCWSRNMKD
         ********:*****************************.******.****

hCLF-1   LTCRWTPGAHGETFLHTNYSLKYKLRWYGQDNTCEEYHTVGPHSCHIPKD
mCLF-1   LTCRWTPGAHGETFLHTNYSLKYKLRWYGQDNTCEEYHTVGPHSCHIPKD
         **************************************************

hCLF-1   LALFTPYEIWVEATNRLGSARSDVLTLDILDVVTTDPPPDVHVSRVGGLE
mCLF-1   LALFTPYEIWVEATNRLGSARSDVLTLDVLDVVTTDPPPDVHVSRVGGLE
         ****************************:*********************

hCLF-1   DQLSVRWVSPPALKDFLFQAKYQIRYRVEDSVDWKVVDDVSNQTSCRLAG
mCLF-1   DQLSVRWVSPPALKDFLFQAKYQIRYRVEDSVDWKVVDDVSNQTSCRLAG
         **************************************************

hCLF-1   LKPGTVYFVQVRCNPFGIYGSKKAGIWSEWSHPTAASTPRSERPGPGGGA
mCLF-1   LKPGTVYFVQVRCNPFGIYGSKKAGIWSEWSHPTAASTPRSERPGPGGGV
         *************************************************.

hCLF-1   CEPRGGEPSSGPVRRELKQFLGWLKKHAYCSNLSFRLYDQWRAWMQKSHK
mCLF-1   CEPRGGEPSSGPVRRELKQFLGWLKKHAYCSNLSFRLYDQWRAWMQKSHK
         **************************************************

hCLF-1   TRNQ---VLPDKL---------
mCLF-1   TRNQDEGILPSGRRGAARGPAG
         ****   :**.
```

Standard domains of the human CLF-1 receptor sequence correspond approximately to: signal from 1 to about 38; first IG-like domain from about residue 39 to 130; a second domain from about 131. to about 237; and the last from about 238 to the end.

The descriptions below may also be applied to the CLF-1, or to the IL-B60/CLF-1 complex. A fusion of the IL-B60 with CLF-1 may be constructed, as, e.g., the hyper IL-6. See, e.g., Fischer, et al. (1997) *Nature Biotechnol.* 15:142-145; Rakemann, et al. (1999) *J. Biol. Chem.* 274:1257-1266; and Peters, et al.(1998) *J. Immunol.* 161:3575-3581; which are incorporated herein by reference.

The original discovery and molecular characterization of CNTF as a potent survival factor for neuronal cells (see, e.g., Hughes, et al. (1988) *Nature* 335:70-73; and Stockli, et al. (1989) *Nature* 342:920-923) suggested a prospective therapeutic use as a molecule that could speed repair of damaged or severed motor neurons (Sendtner, et al. (1990) *Nature* 345: 440-441; and Curtis, et al. (1993) *Nature* 365:253-256) or prevent nerve degeneration (Sendtner, et al. (1992) *Nature* 358:502-504; Emerich, et al. (1997) *Nature* 386:395-399; and Gravel, et al. (1997) *Nature Med.* 3:765-770). However, CNTF is oddly a protein without a secretory signal peptide, and does not appear to escape the cell (Stockli, et al., ibid); furthermore, engineered (Masu, et al. (1993) *Nature* 365:27-32) or naturally occurring (Takahashi, et al. (1994) *Nature Genet.* 7:79-84) disruptions of the CNTF gene are not deleterious. By contrast, gene disruptions of the primary receptor for CNTF (CNTF-Rα) prove lethal shortly after birth. DeChiara, et al. (1995) *Cell* 83:313-322). Together, these observations point to the existence of a second ligand for CNTF-Rα that is physiologically responsible for the in vitro observed, or in vivo desired, actions of CNTF. This work demonstrates that the composite cytokine IL-B60/CLF-1 is likely this long sought-after factor that is both developmentally critical, it is secreted from target organs and directs their innervation by motor neurons, as well as therapeutically promising, since nerve transection results in a fast and. long lasting induction of both IL-B60 and CLF-1, indicating a role for the complex in regeneration. In support of this model, gene disruption of CLF-1 (Alexander, et al. (1999) *Curr. Biol.* 9:605-608) is quite similar in phenotype to the CNTF-Rα knock-out.

In an intriguing twist, while IL-B60 has a signal peptide, its secretion remains critically dependent on complexing with CLF-1, as described. Once secreted, IL-B60 signals via a tripartite receptor system that is otherwise identical to that of CNTF, consisting of the two ubiquitously expressed signal-transducing components gp130 and LIF-R, and the specificity-determining receptor, CNTF-Rα. Strikingly, the role of CLF-1 seems to be restricted to that of a chaperone, since it is discarded from the signaling complex after delivering IL-B60 to CNTF-Rα; indeed, the requirement for CLF-1 can be side-stepped by fusing IL-B60 directly to a soluble form of the CNTF-Rα chain. All three protein chains involved in this novel system, IL-B60, CLF-1, and CNTF-Rα, represent the most highly conserved sequences in the hematopoietic cytokine/receptor superfamily, indicating an evolutionarily critical interaction. Furthermore, the conditional use of a hematopoietic receptor as a secretion factor and escort presents a novel paradigm for cytokine activity.

To summarize, this work sheds light on the entwined biological function of two orphan molecules, IL-B60 and CLF-1, by describing their novel engagement of the CNTF receptor complex. In doing so, we present a strong argument that it is IL-B60/CLF-1 cytokine that serves as a key physiological factor in motor neuron development and regeneration.

II. Purified IL-B60 or Complex

Human IL-B60 amino acid sequence, is shown, in one embodiment within SEQ ID NO: 2. Other naturally occurring nucleic acids which encode the protein can be isolated by standard procedures using the provided sequence, e.g., PCR techniques, or by hybridization. These amino acid sequences, provided amino to carboxy, are important in providing sequence information for the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

As used herein, the term "human soluble IL-B60" shall encompass, when used in a protein context, a protein having amino acid sequence corresponding to a soluble polypeptide from SEQ ID NO: 2. Significant fragments thereof will often retain similar functions, e.g., antigenicity. Preferred embodiments comprise a plurality of distinct, e.g., nonoverlapping, segments of the specified length. Typically, the plurality will be at least two, more usually at least three, and preferably 5, 7, or even more. While the length minima may be recited, longer lengths, of various sizes, may be appropriate, e.g., one of length 7, and two of length 12. Similar features apply to polynucleotides.

Binding components, e.g., antibodies, typically bind to an IL-B60 with high affinity, e.g., at least about 100 nM, usually better than about 30 nM, preferably better than about 10 nM, and more preferably at better than about 3 nM. Counterpart proteins will be found in mammalian species other than human, e.g., other primates, ungulates, or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 150, 149, 148, etc., in all practical combinations. Particularly interesting peptides have ends corresponding to structural domain boundaries, e.g., helices A, B, C, and/or D. See Table 1.

The term "binding composition" refers to molecules that bind with specificity to IL-B60, e.g., in an antibody-antigen interaction. The specificity may be more or less inclusive, e.g., specific to a particular embodiment, or to groups of related embodiments, e.g., primate, rodent, etc. Depletion or absorptions can provide desired selectivities. Also provided are compounds, e.g., proteins, which specifically associate with IL-B60, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman, et al. (eds.) *Goodman & Gilman's: The Pharmacological Bases of Therapeutics* (current ed.) Pergamon Press.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein. In other instances, a harsh detergent may be used to effect significant denaturation.

An IL-B60 polypeptide that specifically binds to or that is specifically immunoreactive with an antibody, e.g., such as a polyclonal antibody, generated against a defined immunogen, e.g., such as an immunogen consisting of an amino acid sequence of SEQ ID NO: 2 or fragments thereof or a polypeptide generated from the nucleic acid of SEQ ID NO: 1 is typically determined in an immunoassay. Included within the metes and bounds of the present invention are those nucleic acid sequences described herein, including functional variants, that encode polypeptides that selectively bind to polyclonal antibodies generated against the prototypical IL-B60 polypeptide as structurally and functionally defined herein. The immunoassay typically uses a polyclonal antiserum which was raised, e.g., to a protein of SEQ ID NO: 2. This antiserum is selected, or depleted, to have low crossreactivity against appropriate other closely related family members, preferably from the same species, and any such crossreactivity is removed by immunoabsorption or depletion prior to use in the immunoassay. Appropriate selective serum preparations can be isolated, and characterized.

In order to produce antisera for use in an immunoassay, the protein, e.g., of SEQ ID NO: 2, is isolated as described herein. For example, recombinant protein may be produced in a mammalian cell line. An appropriate host, e.g., an inbred strain of mice such as Balb/c, is immunized with the protein of SEQ ID NO: 2 using a standard adjuvant, such as Freund's adjuvant, and a standard mouse immunization protocol (see Harlow and Lane). Alternatively, a substantially full length synthetic peptide derived from the sequences disclosed herein can be used as an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other closely related family members, e.g., LIF, CT-1, CNTF, DIL-40, or other members of the IL-6 family, using a competitive binding immunoassay such as the one described in Harlow and Lane, supra, at pages 570-573. Preferably at least two IL-6/IL-12 family members are used in this determination in conjunction with the target. These long chain cytokine family members can be produced as recombinant proteins and isolated using standard molecular biology and protein chemistry techniques as described herein. Thus, antibody preparations can be identified or produced having desired selectivity or specificity for subsets of IL-B60 family members. Alternatively, antibodies may be prepared which bind to the complex comprising the IL-B60 with the CLF-1.

Immunoassays in the competitive binding format can be used for the crossreactivity determinations. For example, the protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein. In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of, e.g., SEQ ID NO: 2 that is required, then the second protein is said to specifically bind to an antibody generated to the immunogen.

III. Physical Variants

This invention also encompasses proteins or peptides having substantial amino acid sequence identity with the amino acid sequence of the IL-B60 antigen. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443-453; Sankoff, et al. (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. Typical homologous proteins or peptides will have from 25-100% identity (if gaps can be introduced), to 50-100% identity (if conservative substitutions are included) with the amino acid sequence of the IL-B60. Identity measures will be at least about 35%, generally at least about 40%, often at least about 50%, typically at least about 60%, usually at least about 70%, preferably at least about 80%, and more preferably at least about 90%.

The isolated IL-B60 DNA can be readily modified by nucleotide substitutions, nucleotide deletions, nucleotide insertions, and inversions of short nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-B60" encompasses a polypeptide otherwise falling within the sequence identity definition of the IL-B60 as set forth above, but having an amino acid sequence which differs from that of IL-B60 as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the natural full length disclosed sequences. Full length sequences will typically be preferred, though truncated versions will also be useful, likewise, genes or proteins found from natural sources are typically most desired. Similar concepts apply to different IL-B60 proteins, particularly those found in various warm blooded animals, e.g., mammals and birds. These descriptions are generally meant to encompass all IL-B60 proteins, not limited to the particular primate embodiments specifically discussed.

IL-B60 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol*. 154:367-382. Preferred embodiments include, e.g., 1-fold, 2-fold, 3-fold, 5-fold, 7-fold, etc., preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties. See Table 2. Recognition of the cytokine structure provides important insight into the structure and positions of residues which may be modified to effect desired changes in receptor interaction. Also, the interaction of the IL-B60 with the CLF-1 protein requires complementary structural features in the interacting surface.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330-1336; and O'Dowd, et al. (1988) *J. Biol. Chem*. 263:15985-15992.

The phosphoramidite method described by Beaucage and Carruthers (1981) *Tetra. Letts*. 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Structural analysis can be applied to this gene, in comparison to the IL-6 family of cytokines. The family includes, e.g., IL-6, IL-11, IL-12, G-CSF, LIF, OSM, CNTF, and Ob. Alignment of the human and mouse IL-B60 sequences with other members of the IL-6 family should allow definition of structural features. In particular, β-sheet and α-helix residues can be determined using, e.g., RASMOL program, see Bazan, et al. (1996) *Nature* 379:591; Lodi, et al. (1994) *Science* 263: 1762-1766; Sayle and Milner-White (1995) *TIBS* 20:374-376; and Gronenberg, et al. (1991) *Protein Engineering* 4:263-269. See, also, Wilkins, et al. (eds. 1997) *Proteome Research: New Frontiers in Functional Genomics* Springer-Verlag, NY. Preferred residues for substitutions include the surface exposed residues which would be predicted to interact with receptor. Other residues which should conserve function will be conservative substitutions, particularly at position far from the surface exposed residues.

IV. Functional Variants

The blocking of physiological response to IL-B60s may result from the competitive inhibition of binding of the ligand to its receptor.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-B60 analogs.

This invention also contemplates the use of competitive drug screening assays, e.g., where neutralizing antibodies to the cytokine, or receptor binding fragments compete with a test compound.

"Derivatives" of IL-B60 antigens include amino acid sequence mutants from naturally occurring forms, glycosylation variants, and covalent or aggregate conjugates with other chemical moieties. Covalent derivatives can be prepared by linkage of functionalities to groups which are found in IL-B60 amino acid side chains or at the N- or C-termini, e.g., by standard means. See, e.g., Lundblad and Noyes (1988) *Chemical Reagents for Protein Modification*, vols. 1-2, CRC Press, Inc., Boca Raton, Fla.; Hugli (ed. 1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem*. 56:497-534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between IL-B60s and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812-816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1-3, Cold Spring Harbor Laboratory; and Ausubel, et al. (eds. 1993) *Current Protocols in Molecular Biology*, Greene and Wiley, NY. Techniques for synthesis of polypeptides are described, e.g., in Merrifield (1963) *J. Amer. Chem. Soc.* 85:2149-2156; Merrifield (1986) *Science* 232: 341-347; Atherton, et al. (1989) *Solid Phase Peptide Synthesis: A Practical Approach*, IRL Press, Oxford; and Grant (1992) *Synthetic Peptides: A User's Guide*, W. H. Freeman, NY. Refolding methods may be applicable to synthetic proteins.

This invention also contemplates the use of derivatives of IL-B60 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-B60 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-B60 antibodies or an alternative binding composition. The IL-B60 proteins can also be labeled with a detectable group, e.g., for use in diagnostic assays. Purification of IL-B60 may be effected by an immobilized antibody or complementary binding partner, e.g., binding portion of a receptor.

A solubilized IL-B60 or fragment of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', F(ab)2, etc. Purified IL-B60 antigens can also be used as a reagent to detect antibodies generated in response to the presence of elevated levels of the cytokine, which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific domains, e.g., helices A, B, C, or D of the IL-B60, or the Ig domains of the CLF-1.

The present invention contemplates the isolation of additional closely related species variants. Southern and Northern blot analysis will establish that similar genetic entities exist in other mammals. It is likely that IL-B60s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-B60, e.g., either species types or cells which lack-corresponding proteins and exhibit negative background activity. This should allow analysis of the function of IL-B60 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339-1336; and approaches used in O'Dowd, et al. (1988) *J. Biol. Chem.* 263:15985-15992; and Lechleiter, et al. (1990) *EMBO J.* 9:4381-4390.

Intracellular functions would probably involve receptor signaling. However, protein internalization may occur under certain circumstances, and interaction between intracellular components and cytokine may occur. Specific segments of interaction of IL-B60 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-B60 will be pursued. The controlling elements associated with the antigens should exhibit differential physiological, developmental, tissue specific, or other expression patterns. Upstream or downstream genetic regions, e.g., control elements, are of interest.

Structural studies of the IL-B60 antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the IL-B60 proteins, including species, polymorphic, or allelic variants, and fragments thereof, both in their naturally occurring forms and in their recombinant forms. Additionally, antibodies can be raised to IL-B60s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-B60s, or screened for agonistic or antagonistic activity, e.g., mediated through a receptor. Antibodies may be agonistic or antagonistic, e.g., by sterically blocking binding to a receptor. These monoclonal antibodies will usually bind with at least a $K_D$ of about 1 mM, more usually at least about 300 μM, typically at least about 100 μM, more typically at least about 30 μM, preferably at least about 10 μM, and more preferably at least about 3 μM or better.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-B60 protein or its receptors. See, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495-497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029-10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3-55. Conversely, protein can be used for depletion or cross absorptions to prepare selectively specific binding compositions.

Antibodies raised against each IL-B60 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding IL-B60, e.g., from a natural source. Typically, it will be useful in isolating a gene from a mammal, and similar procedures will be applied to isolate genes from other species, e.g., warm blooded animals, such as birds and mammals. Cross hybridization will allow isolation of IL-B60 from the same, e.g., polymorphic variants, or other species. A number of different approaches will be available to successfully isolate a suitable nucleic acid clone.

The purified protein or polypeptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press.

For example, a specific binding composition could be used for screening of an expression library made from a cell line which expresses an IL-B60. Screening of intracellular expression can be performed by various staining or immunofluorescence procedures. Binding compositions could be used to affinity purify or sort out cells expressing a surface fusion protein.

The peptide segments can also be used to predict appropriate oligonucleotides to screen a library. The genetic code can be used to select appropriate oligonucleotides useful as probes for screening. See, e.g., SEQ ID NO: 1. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode a biologically active corresponding IL-B60 polypeptide, particularly lacking the portion coding the untranslated portions of the described sequence. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2, particularly a mature, secreted-polypeptide. Further, this invention covers the use of isolated or recombinant DNA, or fragments thereof, which encode proteins which exhibit high identity to a secreted IL-B60. The isolated DNA can have the respective regulatory sequences in the 5' and 3' flanks, e.g., promoters, enhancers, poly-A addition signals, and others. Alternatively, expression may be effected by operably linking a coding segment to a heterologous promoter, e.g., by inserting a promoter upstream from an endogenous gene.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc.

A DNA which codes for an IL-B60 protein will be particularly useful to identify genes, mRNA, and cDNA species which code for related or similar proteins; as well as DNAs which code for homologous proteins from different species. There will be homologs in other species, including primates, rodents, canines, felines, and birds. Various IL-B60 proteins should be homologous and are encompassed herein. However, even proteins that have a more distant evolutionary relationship to the antigen can readily be isolated under appropriate conditions using these sequences if they are sufficiently homologous. Primate IL-B60 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502-1504; Travis (1992) *Science* 256:1392-1394; Kuhn, et al. (1991) *Science* 254:707-710; Capecchi (1989) *Science* 244:1288; Robertson (ed. 1987) *Teratocarcinomas and Embryonic Stem Cells: A Practical Approach*, IRL Press, Oxford; and Rosenberg (1992) *J. Clinical Oncology* 10:180-199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-B60, e.g., in SEQ ID NO: 1. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa (1984) *Nuc. Acids Res*. 12:203-213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson (1968) *J. Mol. Biol*. 31:349-370. Hybridization under stringent conditions should give background of at least 2-fold over background, preferably at least 3-5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math*. 2:482, by the homology alignment algorithm of Needleman and Wunsch (1970) *J. Mol. Biol*. 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403-410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

IL-B60 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making IL-B60 or Complex; Mimetics

DNA which encodes the IL-B60 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161-170; Gubler and Hoffman (1983) *Gene* 25:263-269; and Glover (ed. 1984) *DNA Cloning: A Practical Approach*, IRL Press, Oxford. Alternatively, the sequences provided herein provide useful PCR primers or allow synthetic or other preparation of suitable genes encoding an IL-B60; including naturally occurring embodiments.

This DNA can be expressed in a wide variety of host cells for the synthesis of a full-length IL-B60 or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (eds. 1988) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez, et al., Chapter 10, pp. 205-236; Balbas and Bolivar (1990) *Methods in Enzymology* 185:14-37; and Ausubel, et al. (1993) *Current Protocols in Molecular Biology*, Greene and Wiley, NY.

Representative examples of suitable expression vectors include pCDNA1; pCD, see Okayama, et al. (1985) *Mol. Cell Biol.* 5:1136-1142; pMC1neo Poly-A, see Thomas, et al. (1987) *Cell* 51:503-512; and a baculovirus vector such as pAC 373 or pAC 610. See, e.g., Miller (1988) *Ann. Rev. Microbiol.* 42:177-199.

It will often be desired to express an IL-B60 polypeptide in a system which provides a specific or defined glycosylation pattern. See, e.g., Luckow and Summers (1988) *Bio/Technology* 6:47-55; and Kaufman (1990) *Meth. Enzymol.* 185:487-511.

The IL-B60, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427-454; Tse, et al. (1985) *Science* 230:1003-1008; and Brunner, et al. (1991) *J. Cell Biol.* 114:1275-1283.

Now that the IL-B60 has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Villafranca (ed. 1991) *Techniques in Protein Chemistry II*, Academic Press, San Diego, Calif.

VIII. Uses

The present invention provides reagents which will find use in diagnostic applications as described elsewhere herein, e.g., in IL-B60 mediated conditions, or below in the description of kits for diagnosis. The gene may be useful in forensic sciences, e.g., to distinguish rodent from human, or as a marker to distinguish between different cells exhibiting differential expression or modification patterns. The provided compositions are useful reagents for, e.g., in vitro assays, scientific research, and the synthesis or manufacture of nucleic acids, polypeptides, or antibodies.

This invention also provides reagents with significant commercial and/or therapeutic potential. The IL-B60 (naturally occurring or recombinant), fragments thereof, and antibodies thereto, along with compounds identified as having binding affinity to IL-B60, should be useful as reagents for teaching techniques of molecular biology, immunology, or physiology. Appropriate kits may be prepared with the reagents, e.g., in practical laboratory exercises in production or use of proteins, antibodies, cloning methods, histology, etc.

The reagents will also be useful in the treatment of conditions associated with abnormal physiology or development, including inflammatory conditions. They may be useful in vitro tests for presence or absence of interacting components, which may correlate with success of particular treatment strategies. In particular, modulation of physiology of various, e.g., hematopoietic or lymphoid, cells will be achieved by appropriate methods for treatment using the compositions provided herein. See, e.g., Thomson (1994; ed.) *The Cytokine Handbook* (2d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

For example, a disease or disorder associated with abnormal expression or abnormal signaling by an IL-B60 should be a likely target for an agonist or antagonist. The new cytokine should play a role in regulation or development of hematopoietic cells, e.g., lymphoid cells, which affect immunological responses, e.g., inflammation and/or autoimmune disorders. Alternatively, it may affect vascular physiology or development, or neuronal effects.

In particular, the cytokine should mediate, in various contexts, cytokine synthesis by the cells, proliferation, etc. Antagonists of IL-B60, such as mutein variants of a naturally occurring form of IL-B60 or blocking antibodies, may provide a selective and powerful way to block immune responses, e.g., in situations as inflammatory or autoimmune responses. See also Samter, et al. (eds.) *Immunological Diseases* vols. 1 and 2, Little, Brown and Co.

In addition, certain combination compositions would be useful, e.g., with other modulators of inflammation. Such other molecules may include steroids, other versions of IL-6 and/or G-CSF, including species variants, or viral homologs, and their respective antagonists.

Various abnormal conditions are known in each of the cell types shown to produce IL-B60 mRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve activation by macrophages or monocytes, and many of these will be responsive to treatment by an agonist or antagonist provided herein. See, e.g., Stites and Terr (eds.; 1991) *Basic and Clinical Immunology* Appleton and Lange, Norwalk, Conn.; and Samter, et al. (eds.) *Immunological Diseases* Little, Brown and Co. These problems should be susceptible to prevention or treatment using compositions provided herein. The pancreatic islet localization suggests a possible relevance to diabetes.

IL-B60, antagonists, antibodies, etc., can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-B60 or fragments thereof can be performed to identify compounds having binding affinity to or other relevant biological effects on IL-B60 functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of IL-B60. This invention further contemplates the therapeutic use of blocking antibodies to IL-B60 as antagonists and of stimulatory antibodies as agonists. This approach should be particularly useful with other IL-B60 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for *in situ* administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527-1533.

IL-B60, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Penn.; Avis, et al. (eds. 1993) *Pharmaceutical Dosage Forms: Parenteral Medications*, Dekker, New York; Lieberman, et al. (eds. 1990) *Pharmaceutical Dosage Forms: Tablets*, Dekker, New York; and Lieberman, et al. (eds. 1990) *Pharmaceutical Dosage Forms: Disperse Systems*, Dekker, New York. The therapy of this invention may be combined with or used in association with other agents, e.g., other cytokines, including IL-6 or G-CSF, or their respective antagonists.

Both naturally occurring and recombinant forms of the IL-B60s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble IL-B60 as provided by this invention.

Other methods can be used to determine the critical residues in IL-B60-IL-B60 receptor interactions. Mutational analysis can be performed, e.g., see Somoza, et al. (1993) *J. Exptl. Med.* 178:549-558, to determine specific residues critical in the interaction and/or signaling. PHD (Rost and Sander (1994) *Proteins* 19:55-72) and DSC (King and Sternberg (1996) *Protein Sci.* 5:2298-2310) can provide secondary structure predictions of α-helix (H), β-strand (E), or coil (L). Helices A and D are most important in receptor interaction, with the D helix the more important region. See Table 2.

For example, antagonists can normally be found once the antigen has been structurally defined, e.g., by tertiary structure data. Testing of potential interacting analogs is now possible upon the development of highly automated assay methods using a purified IL-B60. In particular, new agonists and antagonists will be discovered by using screening techniques described herein. Of particular importance are compounds found to have a combined binding affinity for a spectrum of IL-B60 molecules, e.g., compounds which can serve as antagonists for species variants of IL-B60.

One method of drug screening utilizes eukaryotic or prokaryotic host cells which are stably transformed with recombinant DNA molecules expressing an IL-B60. Cells may be isolated which express an IL-B60 in isolation from other molecules. Such cells, either in viable or fixed form, can be used for standard binding partner binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses.

Another technique for drug screening involves an approach which provides high throughput screening for compounds having suitable binding affinity to an IL-B60 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-B60, and washed. The next step involves detecting bound IL-B60.

Rational drug design may also be based upon structural studies of the molecular shapes of the IL-B60 and other effectors or analogs. Effectors may be other proteins which mediate other functions in response to binding, or other proteins which normally interact with IL-B60, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against other cytokine-receptor models. For a detailed description of protein structural determination, see, e.g., Blundell and Johnson (1976) *Protein Crystallography*, Academic Press, New York.

IX. Kits

This invention also contemplates use of IL-B60 proteins, fragments thereof, peptides, and their fusion products in a variety of diagnostic kits and methods for detecting the presence of another IL-B60 or binding partner. Typically the kit will have a compartment containing either a defined IL-B60 peptide or gene segment or a reagent which recognizes one or the other, e.g., IL-B60 fragments or antibodies.

A kit for determining the binding affinity of a test compound to an IL-B60 would typically comprise a test compound; a labeled compound, for example a binding partner or antibody having known binding affinity for IL-B60; a source of IL-B60 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the IL-B60 signaling pathway. The availability of recombinant IL-B60 polypeptides also provide well defined standards for calibrating such assays.

A preferred kit for determining the concentration of, e.g., an IL-B60 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the IL-B60. Compartments containing reagents, and instructions, will normally be provided.

Antibodies, including antigen binding fragments, specific for the IL-B60 or fragments are useful in diagnostic applications to detect the presence of elevated levels of IL-B60 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1-525; Harlow and Lane (1980) *Antibodies: A Laboratory Manual*, CSH Press, NY; and Coligan, et al. (eds. 1993) *Current Protocols in Immunology*, Greene and Wiley, NY.

Anti-idiotypic antibodies may have similar use to diagnose presence of antibodies against an IL-B60, as such may be diagnostic of various abnormal states. For example, overproduction of IL-B60 may result in production of various immunological reactions which may be diagnostic of abnormal physiological states, particularly in proliferative cell conditions such as cancer or abnormal activation or differentiation. Moreover, the distribution pattern available provides information that the cytokine is expressed in pancreatic islets, suggesting the possibility that the cytokine may be involved in function of that organ, e.g., in a diabetes relevant medical condition.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled IL-B60 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, IL-B60, or antibodies thereto can be labeled either directly or indirectly. Possibilities for direct labeling include label groups: radiolabels such as $^{125}I$, enzymes such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free IL-B60, or alternatively the bound from the free test compound. The IL-B60 can be immobilized on various matrixes followed by washing. Suitable matrixes include plastic such as an ELISA plate, filters, and beads. See, e.g., Coligan, et al. (eds. 1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-B60. These sequences can be used as probes for detecting levels of the IL-B60 message in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381-4385; Caskey (1987) *Science* 236:962-967; and Wilchek et al. (1988) *Anal. Biochem.* 171:1-32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97. Other kits may be used to evaluate other cell subsets.

X. Isolating a IL-B60 Receptor

Having isolated a ligand of a specific ligand-receptor interaction, methods exist for isolating the receptor. See, Gearing, et al. (1989) *EMBO J.* 8:3667-3676. For example, means to label the IL-B60 cytokine without interfering with the binding to its receptor can be determined. For example, an affinity label can be fused to either the amino- or carboxyl-terminus of the ligand. Such label may be a FLAG epitope tag, or, e.g., an Ig or Fc domain. An expression library can be screened for specific binding of the cytokine, e.g., by cell sorting, or other screening to detect subpopulations which express such a binding component. See, e.g., Ho, et al. (1993) *Proc. Nat'l Acad. Sci. USA* 90:11267-11271; and Liu, et al. (1994) *J. Immunol.* 152:1821-29. Alternatively, a panning method may be used. See, e.g., Seed and Aruffo (1987) *Proc. Nat'l Acad. Sci. USA* 84:3365-3369.

Protein cross-linking techniques with label can be applied to isolate binding partners of the IL-B60 cytokine. This would allow identification of proteins which specifically interact with the cytokine, e.g., in a ligand-receptor like manner.

Early experiments will be performed to determine whether the known IL-6 or G-CSF receptor components are involved in response(s) to IL-B60. It is also quite possible that these functional receptor complexes may share many or all components with an IL-B60 receptor complex, either a specific receptor subunit or an accessory receptor subunit.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual (*2d ed.) Vols. 1-3, CSH Press, NY; Ausubel, et al. *Biology* Greene Publishing Associates, Brooklyn, N.Y.; Ausubel, et al. (1987 and Supplements) *Current Protocols in Molecular Biology* Wiley/Greene, NY.; Innis, et al. (eds. 1990) *PCR Protocols: A Guide to Methods and Applications* Academic Press, NY; Bonifacino, et al. *Current Protocols in Cell Biology* Wiley, NY.; and Doyle, et al. *Cell and Tissue Culture: Laboratory Protocols* Wiley, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; Matsudaira (ed. 1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress: The High Level Expression & Protein Purification System* QUIAGEN, Inc., Chatsworth, Calif.

Computer sequence analysis is performed, e.g., using available software programs, including those from the University of Wisconsin Genetics Computer Group (GCG), Madison, Wis., the NCBI at NIH, and GenBank, NCBI, EMBO, and other sources of public sequence. Other analysis sources include, e.g., RASMOL program, see Bazan, et al. (1996) *Nature* 379:591; Lodi, et al. (1994) *Science* 263:1762-1766; Sayle and Milner-White (1995) *TIBS* 20:374-376; and Gronenberg, et al. (1991) *Protein Engineering* 4:263-269; and DSC, see King and Sternberg (1996) *Protein Sci.* 5:2298-2310. See, also, Wilkins, et al. (eds. 1997) *Proteome Research: New Frontiers in Functional Genomics* Springer-Verlag, NY.; Salzberg, et al. (eds. 1998) *Computational Methods in Molecular Biology* Elsevier, NY.; and Birren, et al. (eds. 1997) *Genome Analysis: A Laboratory Manual* Cold Spring Harbor Press, Cold Spring Harbor, N.Y.

Standard immunological techniques are described, e.g., in Hertzenberg, et al. (eds. 1996) *Weir's Handbook of Experimental Immunology* vols. 1-4, Blackwell Science; Coligan (1991 and updates) *Current Protocols in Immunology* Wiley/Greene, NY.; and *Methods in Enzymology* vols. 70, 73, 74, 84, 92, 93, 108, 116, 121, 132, 150, 162, and 163. Cytokine assays are described, e.g., in Thomson (ed. 1994) *The Cytokine Handbook* (2d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069-1078), monocyte adhesion to vascular epithelium (see McEvoy, et al. (1997) *J. Exp. Med.* 185:2069-2077), etc. See also Ross (1993) *Nature* 362:801-809; Rekhter and Gordon (1995) *Am. J. Pathol.* 147:668-677; Thyberg, et al. (1990) *Atherosclerosis* 10:966-990; and Gumbiner (1996) *Cell* 84:345-357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cloning of Human IL-B60

The sequence of the gene is provided in Table 1. The sequence is derived from a genomic human sequence. These sequences allow preparation of PCR primers, or probes, to determine cellular distribution of the gene. The sequences allow isolation of genomic DNA which encode the message.

Using the probe or PCR primers, various tissues or cell types are probed to determine cellular distribution. PCR products are cloned using, e.g., a TA cloning kit (Invitrogen). The resulting cDNA plasmids are sequenced from both termini on an automated sequencer (Applied Biosystems).

III. Cellular Expression of IL-B60

An appropriate probe or primers specific for cDNA encoding primate IL-B60 are prepared. Typically, the probe is labeled, e.g., by random priming. The expression is probably in the cell types described, and perhaps also in pancreatic islets.

The presence of a leader sequence led to the expectation of finding IL-B60 secreted when expressed in mammalian cells. Transfection of 293T cells with a tagged form of hIL-B60 (hIL-B60-Etag) did not result in efficient secretion of IL-B60. Instead, IL-B60 could only be immunoprecipitated from the lysate of the transfected cells. The possibility was investigated of IL-B60 being a composite factor like IL-12 (p35/p40) and thus needing a partner for secretion. Among the non-signaling receptors of the IL-6 family the recently described and, thus far, orphan, receptor CLF-1 (NR6) also showed high level of homology between human and murine forms (>95% amino acid identity). Based on these observations a hypothesis was generated that the IL-B60 and CLF-1 are partners.

Southern Analysis: DNA (5 μg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation can include, e.g., peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); CD28-T cell clone; Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+GM-CSF, TNFα 12 days, resting (D101); DC 70% CD1a+, from CD34+GM-CSF, TNFα 12 days, activated with PMA and ionomycin for 1 hr (D102); DC 70% CD1a+, from CD34+GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); epithelial cells, unstimulated; epithelial cells, IL-1β activated; lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102). Expression of IL-B60 transcript was very high in elutriated monocytes, activated with LPS, IFNγ, anti-IL-10 for 4, 16 h pooled (M106); elutriated monocytes, activated with LPS, IFNγ, anti-IL-10 for 1, 2, 6, 12, 24 h pooled (M102); elutriated monocytes, activated LPS for 6 h (M109); and elutriated monocytes, activated LPS for 1 h (M108).

Samples for mouse mRNA expression can include, e.g., resting mouse fibroblastic L cell line (C200); Braf:ER (Braf fusion to estrogen receptor) transfected cells, control (C201); Mel14+ naive T cells from spleen, resting (T209); Mel14+ naive T cells from spleen, stimulated with IFNγ, IL-12, and anti IL-4 to polarize to TH1 cells, exposed to IFNγ and IL-4 for 6, 12, 24 h, pooled (T210); Mel14+ naive T cells from spleen, stimulated with IL-4 and anti IFNγ to polarize to Th2 cells, exposed to IL-4 and anti IFNγ for 6, 13, 24 h, pooled (T211); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized 3× from transgenic Balb/C (see Openshaw; et al. (1995) *J. Exp. Med.* 182:1357-1367; activated with anti-CD3 for 2, 6, 24 h pooled; T202); T cells, highly TH2 polarized 3× from transgenic Balb/C (activated with anti-CD3 for 2, 6, 24 h pooled (T203); T cells, highly TH1 polarized 3× from transgenic C57 bl/6 (activated with anti-CD3 for 2, 6, 24 h pooled; T212); T cells, highly TH2 polarized 3× from transgenic C57 bl/6 (activated with anti-CD3 for 2, 6, 24 h pooled; T213); T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled); CD44-CD25+ pre T cells, sorted from thymus (T204); TH1 T cell clone D1.1, resting for 3 weeks after last stimulation with antigen (T205); TH1 T cell clone D1.1, 10 μg/ml ConA stimulated 15 h (T206); TH2 T cell clone CDC35, resting for 3 weeks after last stimulation with antigen (T207); TH2 T cell clone CDC35, 10 μg/ml ConA stimulated 15 h (T208); unstimulated B cell line CH12 (B201); unstimulated mature B cell leukemia cell line A20 (B200); unstimulated large B cells from spleen (B202); B cells from total spleen, LPS activated (B203); metrizamide enriched dendritic cells from spleen, resting (D200); dendritic cells from bone marrow, resting (D201); unstimulated bone marrow derived dendritic cells depleted with anti B220, anti CD3, and anti Class II, cultured in GM-CSF and IL-4 (D202); bone marrow derived dendritic cells depleted with anti B220, anti CD3, and anti Class II, cultured in GM-CSF and IL-4, stimulated with anti CD40 for 1, 5 d, pooled (D203); monocyte cell line RAW 264.7 activated with LPS 4 h (M200); bone-marrow macrophages derived with GM and M-CSF (M201); bone-marrow macrophages derived with GM-CSF, stimulated with LPS, IFNγ, and IL-10 for 24 h (M205); bone-marrow macrophages derived with GM-CSF, stimulated with LPS, IFNγ, and anti IL-10 for 24 h (M206); peritoneal macrophages (M207); macrophage cell line J774, resting (M202); macrophage cell line J774+LPS+anti-IL-10 at 0.5, 1, 3, 6, 12 h pooled (M203); macrophage cell line J774+LPS+IL-10 at 0.5, 1, 3, 5, 12 h pooled (M204); unstimulated mast cell lines MC-9 and MCP-12 (M208); immortalized endothelial cell line derived from brain microvascular endothelial cells, unstimulated (E200); immortalized endothelial cell line derived from brain microvascular endothelial cells, stimulated overnight with TNFα (E201); immortalized endothelial cell line derived from brain microvascular endothelial cells, stimulated overnight with TNFα (E202); immortalized endothelial cell line derived from brain microvascular endothelial cells, stimulated overnight with TNFα and IL-10 (E203); total aorta from wt C57 bl/6 mouse; total aorta from 5 month ApoE KO mouse (X207); total aorta from 12 month ApoE KO mouse (X207); wt thymus (0214); total thymus, rag-1 (0208); total kidney, rag-1 (0209); total kidney, NZ B/W mouse; and total heart, rag-1 (0202).

The human IL-B60 was found expressed in T cells; the Th0 clone Mot72 (activated); activated PBL; monocytes; dendritic cells; fetal lung, and heavy smoker lung samples.

The CLF-1 was found expressed in dendritic cells; splenocytes; Th1 cells; fetal lung; and lung samples. This distribution is consistent with the complex being important in immune function, e.g., dendritic and immune cells, and in lung physiology.

Since CLF-1 is necessary for IL-B60 secretion in vitro, various human and mouse cDNA libraries were screened for co-expression of both mRNAs. Highest expression for both was found in adult human splenocytes, T cells, activated monocytes and dendritic cells and in fetal lung, and uterus. In mouse libraries, co-expression was strongest in adult lung.

IV. Chromosome Mapping of IL-B60

An isolated cDNA encoding the IL-B60 is used. Chromosome mapping is a standard technique. See, e.g., BIOS Laboratories (New Haven, Conn.) and methods for using a mouse somatic cell hybrid panel with PCR.

The human IL-B60 gene has been localized to human chromosome 11.

V. Purification of IL-B60 Protein or Complexes

Multiple transfected cell lines are screened for one which expresses the cytokine at a high level compared with other cells. Alternatively, a recombinant construct with both subunits can be made. Various cell lines are screened and selected for their favorable properties in handling. Natural IL-B60 can be isolated from natural sources, or by expression from a transformed cell using an appropriate expression vector. Purification of the expressed protein or complex is achieved by standard procedures, or may be combined with engineered means for effective purification at high efficiency from cell lysates or supernatants. FLAG or His6 segments can be used for such purification features. Alternatively, affinity chromatography may be used with specific antibodies, see below.

Protein is produced in coli, insect cell, or mammalian expression systems, as desired.

VI. Isolation of Homologous IL-B60 Genes

The IL-B60 cDNA, or other species counterpart sequence, can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against human IL-B60 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, purification, or diagnosis, as described.

VII. Antibodies Specific for IL-B60 or Complexes

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods. Immunoselection, immunodepletion, and related techniques are available to prepare selective reagents, as desired, e.g., for the IL-B60 alone, or the complex between the two subunits.

VIII. IL-B60 and CLF-1 Coprecipitate

A CLF-1-FLAG construct was prepared in an expression vector. An IL-B60Etag (epitope tagged) construct was also prepared. Transient transfection into COS cells either with the IL-B60Etag construct alone, the CLF-1-FLAG construct alone, or both together. Cells were labeled with $^{35}$S methionine. The supernatants and cells were collected.

Upon co-transfection of cells with IL-B60-Etag and soluble receptor CLF-1-Flag, secretion of both ligand and soluble receptor was greatly enhanced. Both could be immunoprecipitated with antibodies against either the ligand (anti Etag) or the receptor (anti Flag), indicating that IL-B60 and CLF-1 form a soluble cytokine/receptor complex similar to IL-12 (p35/p40). See Gubler, et al. (1991) *Proc. Nat'l Acad. Sci. USA* 88:4143-4147; Wolf, et al. (1991) *J. Immunol.* 146:3074-3081. Thus, coexpression with a correct partner will result in a dramatic increase in the secretion of the gene products. Coexpression of IL-B60 with other soluble receptors including Ebi3 (Devergne, et al. (1996) *J. Virol.* 70:1143-1153), IL-12 p40, and sCNTFR (Davis, et al. (1991) Science 253:59-63) did not result in efficient secretion of the ligand.

The supernatants were immunoprecipitated with either anti-FLAG M2 (precipitates CLF-1) or anti-Etag Ab (precipitates IL-B60). In IL-B60Etag transfectants alone, the level of expression in the supernatant detected using the antiEtag antibodies was very low. In contrast, in the double transfectants, the IL-B60Etag and a second labeled band were immunoprecipitated. The second band corresponds to the CLF-1. Thus, the Etag antibody immunoprecipitates both proteins, e.g., they form a complex. In the single transfectant CLF-1FLAG, a little bit of CLF-1FLAG protein is immunoprecipitated with the anti-FLAG M2 Ab. This result is consistent with the other soluble receptors, e.g., for p40 component of IL-12. However, in the double transfectants not only is more CLF-1 seen, but now also IL-B60. The immunoprecipitation works in both directions.

IX. IL-B60 Binds to the CNTFR

To identify the signaling receptors for IL-B60/CLF-1 conditioned medium from hIL-B60 and mCLF-1 cotransfected 293T cells was added to BA/F3 cells stably transfected with human gp130 alone or hgp130 in combination with the hIL-6R, hOSMR, hLIFR, or hLIFR and hCNTFR, respectively. Only BA/F3 cells expressing gp130, LIFR, and CNTFR showed a proliferative response upon stimulation with IL-B60/CLF-1. To analyze the possibility of a signaling complex consisting of CNTFR/gp130 or CNTFR/LIFR only, two soluble fusion proteins were designed connecting either the CNTFR or CLF-1 to IL-B60 via a flexible linker. Similar so-called hyper-cytokines have been shown to be 100-1000× more active on cells than cytokine and soluble receptor added separately. See Fischer, et al. (1997) *Nature Biotechnol.* 15:142-145. Hyper-CNTFR-IL-B60 was able to induce proliferation of BAF3/gp130/LIFR cells but not of BAF3/gp130 cells, showing that the LIFR is a component of the signaling complex. Stimulation of cells with hyper-CLF-1-IL-B60 did not result in proliferation of any cell line. This indicated that although necessary for IL-B60 secretion, CLF-1 is not a subunit of the active signaling receptor complex.

Involvement of gp130 in the active receptor complex was shown with a neutralizing antibody against gp130 which completely blocked this response. Furthermore, analysis of signal transducers in lysates from BA/F3 cells expressing gp130, LIFR, and CNTFR showed that STAT3 is only phosphorylated after stimulation with either co-expressed IL-B60 and CLF-1 or with the CNTFR-IL-B60 fusion protein but not with the CLF-1-IL-B60 fusion.

X. Evaluation of Breadth of Biological Functions

Biological activities of IL-B60 or complex are tested based, e.g., on the sequence and structural homology between IL-B60 and IL-6 and G-CSF. Initially, assays that had shown biological activities of IL-6 or G-CSF are examined.

A. Regulation of IL-B60 and CLF-1 After Sciatic Nerve Injury

IL-B60 and CLF-1 expression in the mouse spinal cord was analyzed in unilateral transection of the sciatic nerve followed by separation of proximal and distal nerve stumps, thus preventing regeneration. At various time points, tissue from the transection area was collected and analyzed by quantitative PCR for expression of IL-B60 and CLF-1. Transection of the sciatic nerve resulted in fast and long lasting upregulation of ligand and receptor. After 6 hrs IL-B60 and CLF-1 were upregulated. Expression was still elevated 20 days after transection when compared to non-lesioned or sham-lesioned nerves. In regenerating axons (crushed nerves) both IL-B60 and CLF-1 are downregulated after 12 h, but whereas IL-B60 expression almost reaches levels of non-lesioned nerves after 20 days, CLF-1 levels peak after 20 days. This might point to an additional function of CLF-1, possibly in remyelination, which starts after two weeks. Transection of the sciatic nerve in mice lacking GM-CSF and a macrophage response in nerve shows that IL-B60 expression after 4 days is not altered compared to normal mice. However, CLF-1 levels in those mice are heterogeneous, with a range from no alteration to an almost 4 fold increase of expression compared to normal littermates.

B. Effects on Proliferation of Cells

The effect on proliferation of various cell types are evaluated with various concentrations of cytokine. A dose response analysis is performed, in combinations with the related cytokines IL-6, G-CSF, etc. A cytosensor machine may be used, which detects cell metabolism and growth (Molecular Devices, Sunnyvale, Calif.).

C. Effects on the Expression of Cell Surface Molecules on Human Monocytes

Monocytes are purified by negative selection from peripheral blood mononuclear cells of normal healthy donors. Briefly, $3\times10^8$ ficoll banded mononuclear cells are incubated on ice with a cocktail of monoclonal antibodies (Becton-Dickinson; Mountain View, Calif.) consisting, e.g., of 200 μl of αCD2 (Leu-5A), 200 μl of αCD3 (Leu-4), 100 μl of αCD8 (Leu 2a), 100 μl of αCD19 (Leu-12), 100 μl of αCD20 (Leu-16), 100 μl of αCD56 (Leu-19), 100 μl of αCD67 (IOM 67; Immunotech, Westbrook, Me.), and anti-glycophorin antibody (10F7MN, ATCC, Rockville, Md.). Antibody bound cells are washed and then incubated with sheep anti-mouse IgG coupled magnetic beads (Dynal, Oslo, Norway) at a bead to cell ratio of 20:1. Antibody bound cells are separated from monocytes by application of a magnetic field. Subsequently, human monocytes are cultured in Yssel's medium (Gemini Bioproducts, Calabasas, Calif.) containing 1% human AB serum in the absence or presence of IL-B60, IL-6, G-CSF or combinations.

Analyses of the expression of cell surface molecules can be performed by direct immunofluorescence. For example, $2\times10^5$ purified human monocytes are incubated in phosphate buffered saline (PBS) containing 1% human serum on ice for 20 minutes. Cells are pelleted at 200×g. Cells are resuspended in 20 ml PE or FITC labeled mAb. Following an additional 20 minute incubation on ice, cells are washed in PBS containing 1% human serum followed by two washes in PBS alone. Cells are fixed in PBS containing 1% paraformaldehyde and analyzed on FACScan flow cytometer (Becton Dickinson; Mountain View, Calif.). Exemplary mAbs are used, e.g.: CD11b (anti-mac1), CD11c (a gp150/95), CD14 (Leu-M3), CD54 (Leu 54), CD80 (anti-BB1/B7), HLA-DR (L243) from Becton-Dickinson and CD86 (FUN 1; Pharmingen), CD64 (32.2; Medarex), CD40 (mAb89; Schering-Plough France).

D. Effects of IL-B60 or Complex on Cytokine Production by Human Monocytes

Human monocytes are isolated as described and cultured in Yssel's medium (Gemini Bioproducts, Calabasas, Calif.) containing 1% human AB serum in the absence or presence of IL-B60 (1/100 dilution baculovirus expressed material). In addition, monocytes are stimulated with LPS (*E. coli* 0127:B8 Difco) in the absence or presence of IL-B60 and the concentration of cytokines (IL-1β, IL-6, TNFα, GM-CSF, and IL-10) in the cell culture supernatant determined by ELISA.

For intracytoplasmic staining for cytokines, monocytes are cultured (1 million/ml) in Yssel's medium in the absence or presence of IL-B60 and LPS (*E. coli* 0127:B8 Difco) and 10 mg/ml Brefeldin A (Epicentre technologies Madison Wis.) for 12 hrs. Cells are washed in PBS and incubated in 2% formaldehyde/PBS solution for 20 minutes at RT. Subsequently cells are washed, resuspended in permeabilization buffer (0.5% saponin (Sigma) in PBS/BSA (0.5%)/Azide (1 mM)) and incubated for 20 minutes at RT. Cells ($2\times10^5$) are centrifuged and resuspended in 20 ml directly conjugated anti-cytokine mAbs diluted 1:10 in permeabilization buffer for 20 minutes at RT. The following antibodies can be used: IL-1α-PE (364-3B3-14); IL-6-PE (MQ2-13A5); TNFα-PE (MAb11); GM-CSF-PE (BVD2-21C11); and IL-12-PE (C11.5.14; Pharmingen San Diego, Calif.). Subsequently, cells are washed twice in permeabilization buffer and once in PBS/BSA/Azide and analyzed on FACScan flow cytometer (Becton Dickinson; Mountain View, Calif.).

E. Effects of IL-B60 on Proliferation of Human Peripheral Blood Mononuclear Cells (PBMC)

Total PBMC are isolated from buffy coats of normal healthy donors by centrifugation through ficoll-hypaque as described (Boyum, et al.). PBMC are cultured in 200 μl Yssel's medium (Gemini Bioproducts, Calabasas, Calif.) containing 1% human AB serum in 96 well plates (Falcon, Becton-Dickinson, N.J.) in the absence or presence of IL-B60. Cells are cultured in medium alone or in combination with 100 U/ml IL-2 (R&D Systems) for 120 hours. 3H-Thymidine (0.1 mCi) is added during the last six hours of culture and 3H-Thymidine incorporation determined by liquid scintillation counting.

The native, recombinant, and fusion proteins would be tested for agonist and antagonist activity in many other biological assay systems, e.g., on T-cells, B-cells, NK, macrophages, dendritic cells, hematopoietic progenitors, etc. Because of the IL-6 and G-CSF structural relationship, assays related to those activities should be analyzed IL-B60 is evaluated for agonist or antagonist activity on transfected cells expressing IL-6 or G-CSF receptor and controls. See, e.g., Ho, et al. (1993) *Proc. Nat'l Acad. Sci. USA* 90, 11267-11271; Ho, et al. (1995) *Mol. Cell. Biol.* 15:5043-5053; and Liu, et al. (1994). *J. Immunol.* 152:1821-1829.

IL-B60 is evaluated for effect in macrophage/dendritic cell activation and antigen presentation assays, T cell cytokine production and proliferation in response to antigen or allogeneic stimulus. See, e.g., de Waal Malefyt et al. (1991) *J. Exp. Med.* 174:1209-1220; de Waal Malefyt et al. (199.1) *J. Exp. Med.* 174:915-924; Fiorentino, et al. (.1991) *J. Immunol.* 147, 3815-3822; Fiorentino, et al. (1991) *J. Immunol.* 146:3444-3451; and Groux, et al. (1996) *J. Exp. Med.* 184:19-29.

IL-B60 will also be evaluated for effects on NK cell stimulation. Assays may be based, e.g., on Hsu, et al. (1992) *Internat. Immunol.* 4:563-569; and Schwarz, et al. (1994) *J. Immunother*. 16:95-104.

B cell growth and differentiation effects will be analyzed, e.g., by the methodology described, e.g., in Defrance, et al. (1992). *J. Exp. Med.* 175:671-682; Rousset, et al. (1992) *Proc. Nat'l Acad. Sci. USA* 89:1890-1893; including IgG2 and IgA2 switch factor assays. Note that, unlike COS7 supernatants, NIH3T3 and COP supernatants apparently do not interfere with human B cell assays.

F. IL-B60 and CLF-1 Induce a Switch in Neurotransmitter Properties

Cholineric sympathetic neurons innervate at least three different targets: sweat glands, vasculature in skeletal muscle, and periosteum. Mature innervation of sympathetic neurons begins at the end of the first postnatal week and is characterized by the appearance of cholineric properties. Cultures of sympathetic neurons were analyzed for the induction of different neuromodulators, which specify the cholinergic phenotype. Cholecystokinin (CCK), vasoactive intestinal polypeptide (VIP), substance P (SP) and somatostatin (SOM) are upregulated after stimulation of neurons with conditioned medium from IL-B60/CLF-1 cotransfected cells or the CNTFR-IL-B60 fusion protein. Thus, the complex exhibits significant developmental biology function, and may be effective in inducing certain aspects of neural development.

XI. Generation and Analysis of Genetically Altered Animals

Transgenic mice can be generated by standard methods. Such animals are useful to determine the effects of overexpression of the gene, in specific tissues, or completely throughout the organism. Such may provide interesting insight into development of the animal or particular tissues in various stages. Moreover, the effect on various responses to biological stress can be evaluated. See, e.g., Hogan, et al. (1995) *Manipulating the Mouse Embryo: A Laboratory Manual* (2d ed.) Cold Spring Harbor Laboratory Press.

Adenovirus techniques are available for expression of the gene in various cells and organs. See, e.g., Hitt, et al. (1997) *Adv. Pharmacol.* 40:137-195; and literature from Quantum Biotechnologies, Montreal, Canada. Animals may be useful to determine the effects of the gene on various developmental or physiologically functional animal systems.

The genomic structure for the mouse IL-B60 has been determined. A strategy for the production of IL-B60 knockout mice can be developed, and appropriate constructs made.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated soluble cytokine complex comprising the mature forms of SEQ ID NO: 2 and SEQ ID NO: 12.

2. The cytokine complex of claim 1, wherein the cytokine complex binds to a receptor complex comprising human CTNF-R, human gp130, and human LIF-R.

3. The cytokine complex of claim 1, wherein the cytokine complex is attached to at least one detection tag.

4. The cytokine complex of claim 3, wherein the detection tag is selected from the group consisting of FLAG, His6, and Ig domain.

5. A kit comprising the cytokine complex of claim 1, wherein the kit contains:

a) a compartment comprising the cytokine complex; and b) instructions for use or disposal of reagents in the kit.

6. The cytokine complex of claim 1, wherein the cytokine complex induces neuromodulators selected from the group consisting of cholecystokinin (CCK), vasoactive intestinal polypeptide (VIP), substance P (SP), and somatostatin (SOM).

7. A composition comprising the cytokine complex of claim 1 and an aqueous carrier.

8. An isolated soluble cytokine fusion protein comprising a mature form of SEQ ID NO: 2 fused to a mature form of SEQ ID NO: 12.

9. The cytokine fusion protein of claim 8, wherein the cytokine complex binds to a receptor complex comprising human CTNF-R, human gp130, and human LIF-R.

10. The cytokine fusion protein of claim 8, wherein the cytokine complex is attached to at least one detection tag.

11. The cytokine fusion protein of claim 10, wherein the detection tag is selected from the group consisting of FLAG, His6, and Ig domain.

12. A kit comprising the cytokine fusion protein of claim 8, wherein the kit contains:

a) a compartment comprising the cytokine fusion protein; and b) instructions for use or disposal of reagents in the kit.

13. A composition comprising the cytokine fusion protein of claim 8 and an aqueous carrier.

14. The cytokine complex of claim 8, wherein the cytokine fusion protein induces neuromodulators selected from the group consisting of cholecystokinin (CCK), vasoactive intestinal polypeptide (VIP), substance P (SP), and somatostatin (SOM).

* * * * *

SEQUENCE LISTING

```
<160> NUMBER OF SEQ ID NOS: 13

<210> SEQ ID NO 1
<211> LENGTH: 1790
<212> TYPE: DNA
<213> ORGANISM: primate
<220> FEATURE:
<221> NAME/KEY: CDS
<222> LOCATION: (162)..(806)
<220> FEATURE:
<221> NAME/KEY: mat_peptide
<222> LOCATION: (213)..(806)

<400> SEQUENCE: 1

ccgagcgaaa aaaacctgcg agtgggcctg gcggatggga ttattaaagc ttcgccggag      60

ccgcggctcg ccctcccact ccgccagcct ccgggagagg agccgcaccc ggccggcccg     120

gccccagccc catggacctc cgagcagggg actcgtgggg g atg tta gcg tgc ctg     176
                                              Met Leu Ala Cys Leu
                                                      -15

tgc acg gtg ctc tgg cac ctc cct gca gtg cca gct ctc aat cgc aca       224
Cys Thr Val Leu Trp His Leu Pro Ala Val Pro Ala Leu Asn Arg Thr
        -10                 -5                  -1   1

ggg gac cca ggg cct ggc ccc tcc atc cag aaa acc tat gac ctc acc       272
Gly Asp Pro Gly Pro Gly Pro Ser Ile Gln Lys Thr Tyr Asp Leu Thr
  5                  10                  15                  20

cgc tac ctg gag cac caa ctc cgc agc ttg gct ggg acc tat ctg aac       320
```

-continued

```
Arg Tyr Leu Glu His Gln Leu Arg Ser Leu Ala Gly Thr Tyr Leu Asn
                 25                  30                  35

tac ctg ggc ccc cct ttc aac gag cca gac ttc aac cct ccc cgc ctg       368
Tyr Leu Gly Pro Pro Phe Asn Glu Pro Asp Phe Asn Pro Pro Arg Leu
             40                  45                  50

ggg gca gag act ctg ccc agg gcc act gtt gac ttg gag gtg tgg cga       416
Gly Ala Glu Thr Leu Pro Arg Ala Thr Val Asp Leu Glu Val Trp Arg
         55                  60                  65

agc ctc aat gac aaa ctg cgg ctg acc cag aac tac gag gcc tac agc       464
Ser Leu Asn Asp Lys Leu Arg Leu Thr Gln Asn Tyr Glu Ala Tyr Ser
     70                  75                  80

cac ctt ctg tgt tac ttg cgt ggc ctc aac cgt cag gct gcc act gct       512
His Leu Leu Cys Tyr Leu Arg Gly Leu Asn Arg Gln Ala Ala Thr Ala
 85                  90                  95                 100

gag ctg cgc cgc agc ctg gcc cac ttc tgc acc agc ctc cag ggc ctg       560
Glu Leu Arg Arg Ser Leu Ala His Phe Cys Thr Ser Leu Gln Gly Leu
                105                 110                 115

ctg ggc agc att gcg ggc gtc atg gca gct ctg ggc tac cca ctg ccc       608
Leu Gly Ser Ile Ala Gly Val Met Ala Ala Leu Gly Tyr Pro Leu Pro
            120                 125                 130

cag ccg ctg cct ggg act gaa ccc act tgg act cct ggc cct gcc cac       656
Gln Pro Leu Pro Gly Thr Glu Pro Thr Trp Thr Pro Gly Pro Ala His
        135                 140                 145

agt gac ttc ctc cag aag atg gac gac ttc tgg ctg ctg aag gag ctg       704
Ser Asp Phe Leu Gln Lys Met Asp Asp Phe Trp Leu Leu Lys Glu Leu
    150                 155                 160

cag acc tgg ctg tgg cgc tcg gcc aag gac ttc aac cgg ctc aag aag       752
Gln Thr Trp Leu Trp Arg Ser Ala Lys Asp Phe Asn Arg Leu Lys Lys
165                 170                 175                 180

aag atg cag cct cca gca gct gca gtc acc ctg cac ctg ggg gct cat       800
Lys Met Gln Pro Pro Ala Ala Ala Val Thr Leu His Leu Gly Ala His
                185                 190                 195

ggc ttc tgacttctga ccttctcctc ttcgctcccc cttcaaaccc tgctcccact        856
Gly Phe

ttgtgagagc cagccctgta tgccaacacc tgttgagcca ggagacagaa gctgtgagcc     916

tctggccctt tcctggaccg gctgggcgtg tgatgcgatc agccctgtct cctccccacc     976

tcccaaaggt ctaccgagct ggggaggagg tacagtaggc cctgtcctgt cctgtttcta    1036

caggaagtca tgctcgaggg agtgtgaagt ggttcaggtt ggtgcagagg cgctcatggc    1096

ctcctgcttc ttgcctacca cttggccagt gcccacccag cccctcaggt ggcacatctg    1156

gagggcaggg gttgaggggc caccaccaca catgcctttc tggggtgaag ccctttggct    1216

gccccactct ccttggatgg gtgttgctcc cttatcccca aatcactcta tacatccaat    1276

tcaggaaaca aacatggtgg caattctaca caaaaagaga tgagattaac agtgcagggt    1336

tggggtctgc attggaggtg ccctataaac cagaagagaa aatactgaaa gcacaggggc    1396

agggacagac cagaccagac ccaggagtct ccaaagcaca gagtggcaaa caaaacccga    1456

gctgagcatc aggaccttgc ctcgaattgt cttccagtat tacggtgcct cttctctgcc    1516

ccctttccca gggtatctgt gggttgccag gctggggagg gcaaccatag ccacaccaca    1576

ggatttcctg aaagtttaca atgcagtagc attttggggt gtagggtggc agctccccaa    1636

ggccctgccc cccagcccca cccactcatg actctaagtg tgttgtatta atatttattt    1696

atttggagat gttatttatt agatgatatt tattgcagaa tttctattct tgtattaaca    1756

aataaaatgc ttgccccaga acaaaaaaaa aaaa                                1790
```

-continued

<210> SEQ ID NO 2
<211> LENGTH: 215
<212> TYPE: PRT
<213> ORGANISM: primate

<400> SEQUENCE: 2

```
Met Leu Ala Cys Leu Cys Thr Val Leu Trp His Leu Pro Ala Val Pro
        -15                 -10                 -5

Ala Leu Asn Arg Thr Gly Asp Pro Gly Pro Gly Pro Ser Ile Gln Lys
 -1   1               5                  10                  15

Thr Tyr Asp Leu Thr Arg Tyr Leu Glu His Gln Leu Arg Ser Leu Ala
                 20                  25                  30

Gly Thr Tyr Leu Asn Tyr Leu Gly Pro Pro Phe Asn Glu Pro Asp Phe
             35                  40                  45

Asn Pro Pro Arg Leu Gly Ala Glu Thr Leu Pro Arg Ala Thr Val Asp
         50                  55                  60

Leu Glu Val Trp Arg Ser Leu Asn Asp Lys Leu Arg Leu Thr Gln Asn
     65                  70                  75

Tyr Glu Ala Tyr Ser His Leu Leu Cys Tyr Leu Arg Gly Leu Asn Arg
 80                  85                  90                  95

Gln Ala Ala Thr Ala Glu Leu Arg Arg Ser Leu Ala His Phe Cys Thr
                100                 105                 110

Ser Leu Gln Gly Leu Leu Gly Ser Ile Ala Gly Val Met Ala Ala Leu
            115                 120                 125

Gly Tyr Pro Leu Pro Gln Pro Leu Pro Gly Thr Glu Pro Thr Trp Thr
        130                 135                 140

Pro Gly Pro Ala His Ser Asp Phe Leu Gln Lys Met Asp Asp Phe Trp
    145                 150                 155

Leu Leu Lys Glu Leu Gln Thr Trp Leu Trp Arg Ser Ala Lys Asp Phe
160                 165                 170                 175

Asn Arg Leu Lys Lys Lys Met Gln Pro Pro Ala Ala Ala Val Thr Leu
                180                 185                 190

His Leu Gly Ala His Gly Phe
            195
```

<210> SEQ ID NO 3
<211> LENGTH: 648
<212> TYPE: DNA
<213> ORGANISM: primate
<220> FEATURE:
<221> NAME/KEY: CDS
<222> LOCATION: (1)..(645)
<220> FEATURE:
<221> NAME/KEY: mat_peptide
<222> LOCATION: (52)..(645)

<400> SEQUENCE: 3

```
atg tta gct tgc cta tgc acg gtg ctg tgg cac ctc cct gca gtg cca       48
Met Leu Ala Cys Leu Cys Thr Val Leu Trp His Leu Pro Ala Val Pro
        -15                 -10                 -5

gct ctt aat cgc aca gga gat cca ggc cct ggc ccc tcc atc cag aaa       96
Ala Leu Asn Arg Thr Gly Asp Pro Gly Pro Gly Pro Ser Ile Gln Lys
 -1   1               5                  10                  15

acc tat gac ctc acc cgc tac ctg gag cat caa ctc cgc agc tta gct      144
Thr Tyr Asp Leu Thr Arg Tyr Leu Glu His Gln Leu Arg Ser Leu Ala
                 20                  25                  30

ggg acc tac ctg aac tac ctg ggc ccc cct ttc aac gag cct gac ttc      192
Gly Thr Tyr Leu Asn Tyr Leu Gly Pro Pro Phe Asn Glu Pro Asp Phe
             35                  40                  45
```

-continued

```
aat cct cct cga ctg ggg gca gaa act ctg ccc agg gcc acg gtc aac      240
Asn Pro Pro Arg Leu Gly Ala Glu Thr Leu Pro Arg Ala Thr Val Asn
         50                  55                  60

ttg gaa gtg tgg cga agc ctc aat gac agg ctg cgg ctg acc cag aac      288
Leu Glu Val Trp Arg Ser Leu Asn Asp Arg Leu Arg Leu Thr Gln Asn
     65                  70                  75

tat gag gcg tac agt cac ctc ctg tgt tac ttg cgt ggc ctc aac cgt      336
Tyr Glu Ala Tyr Ser His Leu Leu Cys Tyr Leu Arg Gly Leu Asn Arg
 80                  85                  90                  95

cag gct gcc aca gct gaa ctc cga cgt agc ctg gcc cac ttc tgt acc      384
Gln Ala Ala Thr Ala Glu Leu Arg Arg Ser Leu Ala His Phe Cys Thr
                100                 105                 110

agc ctc cag ggc ctg ctg ggc agc att gca ggt gtc atg gcg acg ctt      432
Ser Leu Gln Gly Leu Leu Gly Ser Ile Ala Gly Val Met Ala Thr Leu
            115                 120                 125

ggc tac cca ctg ccc cag cct ctg cca ggg act gag cca gcc tgg gcc      480
Gly Tyr Pro Leu Pro Gln Pro Leu Pro Gly Thr Glu Pro Ala Trp Ala
        130                 135                 140

cct ggc cct gcc cac agt gac ttc ctc cag aag atg gat gac ttc tgg      528
Pro Gly Pro Ala His Ser Asp Phe Leu Gln Lys Met Asp Asp Phe Trp
    145                 150                 155

ctg ctg aag gag ctg cag acc tgg cta tgg cgt tca gcc aag gac ttc      576
Leu Leu Lys Glu Leu Gln Thr Trp Leu Trp Arg Ser Ala Lys Asp Phe
160                 165                 170                 175

aac cgg ctt aag aag aag atg cag cct cca gca gct tca gtc acc ctg      624
Asn Arg Leu Lys Lys Lys Met Gln Pro Pro Ala Ala Ser Val Thr Leu
                180                 185                 190

cac ttg gag gcc cat ggt ttc tga                                      648
His Leu Glu Ala His Gly Phe
            195


<210> SEQ ID NO 4
<211> LENGTH: 215
<212> TYPE: PRT
<213> ORGANISM: primate

<400> SEQUENCE: 4

Met Leu Ala Cys Leu Cys Thr Val Leu Trp His Leu Pro Ala Val Pro
        -15                 -10                 -5

Ala Leu Asn Arg Thr Gly Asp Pro Gly Pro Gly Pro Ser Ile Gln Lys
 -1   1               5                  10                  15

Thr Tyr Asp Leu Thr Arg Tyr Leu Glu His Gln Leu Arg Ser Leu Ala
                 20                  25                  30

Gly Thr Tyr Leu Asn Tyr Leu Gly Pro Pro Phe Asn Glu Pro Asp Phe
             35                  40                  45

Asn Pro Pro Arg Leu Gly Ala Glu Thr Leu Pro Arg Ala Thr Val Asn
         50                  55                  60

Leu Glu Val Trp Arg Ser Leu Asn Asp Arg Leu Arg Leu Thr Gln Asn
     65                  70                  75

Tyr Glu Ala Tyr Ser His Leu Leu Cys Tyr Leu Arg Gly Leu Asn Arg
 80                  85                  90                  95

Gln Ala Ala Thr Ala Glu Leu Arg Arg Ser Leu Ala His Phe Cys Thr
                100                 105                 110

Ser Leu Gln Gly Leu Leu Gly Ser Ile Ala Gly Val Met Ala Thr Leu
            115                 120                 125

Gly Tyr Pro Leu Pro Gln Pro Leu Pro Gly Thr Glu Pro Ala Trp Ala
        130                 135                 140

Pro Gly Pro Ala His Ser Asp Phe Leu Gln Lys Met Asp Asp Phe Trp
```

-continued

```
    145                 150                 155

Leu Leu Lys Glu Leu Gln Thr Trp Leu Trp Arg Ser Ala Lys Asp Phe
160                 165                 170                 175

Asn Arg Leu Lys Lys Lys Met Gln Pro Pro Ala Ala Ser Val Thr Leu
                180                 185                 190

His Leu Glu Ala His Gly Phe
            195


<210> SEQ ID NO 5
<211> LENGTH: 203
<212> TYPE: PRT
<213> ORGANISM: rodent

<400> SEQUENCE: 5

Met Lys Val Leu Ala Ala Gly Ile Val Pro Leu Leu Leu Leu Val Leu
  1               5                  10                  15

His Trp Lys His Gly Ala Gly Ser Pro Leu Pro Ile Thr Pro Val Asn
            20                  25                  30

Ala Thr Cys Ala Ile Arg His Pro Cys His Gly Asn Leu Met Asn Gln
        35                  40                  45

Ile Lys Asn Gln Leu Ala Gln Leu Asn Gly Ser Ala Asn Ala Leu Phe
     50                  55                  60

Ile Ser Tyr Tyr Thr Ala Gln Gly Glu Pro Phe Pro Asn Asn Val Glu
 65                  70                  75                  80

Lys Leu Cys Ala Pro Asn Met Thr Asp Phe Pro Ser Phe His Gly Asn
                 85                  90                  95

Gly Thr Glu Lys Thr Lys Leu Val Glu Leu Tyr Arg Met Val Ala Tyr
            100                 105                 110

Leu Ser Ala Ser Leu Thr Asn Ile Thr Arg Asp Gln Lys Val Leu Asn
        115                 120                 125

Pro Thr Ala Val Ser Leu Gln Val Lys Leu Asn Ala Thr Ile Asp Val
    130                 135                 140

Met Arg Gly Leu Leu Ser Asn Val Leu Cys Arg Leu Cys Asn Lys Tyr
145                 150                 155                 160

Arg Val Gly His Val Asp Val Pro Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
        195                 200


<210> SEQ ID NO 6
<211> LENGTH: 202
<212> TYPE: PRT
<213> ORGANISM: primate

<400> SEQUENCE: 6

Met Lys Val Leu Ala Ala Gly Val Val Pro Leu Leu Leu Val Leu His
  1               5                  10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
     50                  55                  60

Leu Tyr Tyr Thr Ala Gln Gly Glu Pro Phe Pro Asn Asn Leu Asp Lys
```

-continued 65 70 75 80

Leu Cys Gly Pro Asn Val Thr Asp Phe Pro Pro Phe His Ala Asn Gly
85 90 95

Thr Glu Lys Ala Lys Leu Val Glu Leu Tyr Arg Ile Val Val Tyr Leu
100 105 110

Gly Thr Ser Leu Gly Asn Ile Thr Arg Asp Gln Lys Ile Leu Asn Pro
115 120 125

Ser Ala Leu Ser Leu His Ser Lys Leu Asn Ala Thr Ala Asp Ile Leu
130 135 140

Arg Gly Leu Leu Ser Asn Val Leu Cys Arg Leu Cys Ser Lys Tyr His
145 150 155 160

Val Gly His Val Asp Val Thr Tyr Gly Pro Asp Thr Ser Gly Lys Asp
165 170 175

Val Phe Gln Lys Lys Lys Leu Gly Cys Gln Leu Leu Gly Lys Tyr Lys
180 185 190

Gln Ile Ile Ala Val Leu Ala Gln Ala Phe
195 200

<210> SEQ ID NO 7
<211> LENGTH: 201
<212> TYPE: PRT
<213> ORGANISM: primate

<400> SEQUENCE: 7

Met Ser Arg Arg Glu Gly Ser Leu Glu Asp Pro Gln Thr Asp Ser Ser
1 5 10 15

Val Ser Leu Leu Pro His Leu Glu Ala Lys Ile Arg Gln Thr His Ser
20 25 30

Leu Ala His Leu Leu Thr Lys Tyr Ala Glu Gln Leu Leu Gln Glu Tyr
35 40 45

Val Gln Leu Gln Gly Asp Pro Phe Gly Leu Pro Ser Phe Ser Pro Pro
50 55 60

Arg Leu Pro Val Ala Gly Leu Ser Ala Pro Ala Pro Ser His Ala Gly
65 70 75 80

Leu Pro Val His Glu Arg Leu Arg Leu Asp Ala Ala Ala Leu Ala Ala
85 90 95

Leu Pro Pro Leu Leu Asp Ala Val Cys Arg Arg Gln Ala Glu Leu Asn
100 105 110

Pro Arg Ala Pro Arg Leu Leu Arg Arg Leu Glu Asp Ala Ala Arg Gln
115 120 125

Ala Arg Ala Leu Gly Ala Ala Val Glu Ala Leu Leu Ala Ala Leu Gly
130 135 140

Ala Ala Asn Arg Gly Pro Arg Ala Glu Pro Pro Ala Ala Thr Ala Ser
145 150 155 160

Ala Ala Ser Ala Thr Gly Val Phe Pro Ala Lys Val Leu Gly Leu Arg
165 170 175

Val Cys Gly Leu Tyr Arg Glu Trp Leu Ser Arg Thr Glu Gly Asp Leu
180 185 190

Gly Gln Leu Leu Pro Gly Gly Ser Ala
195 200

<210> SEQ ID NO 8
<211> LENGTH: 203
<212> TYPE: PRT
<213> ORGANISM: rodent

-continued

<400> SEQUENCE: 8

```
Met Ser Gln Arg Glu Gly Ser Leu Glu Asp His Gln Thr Asp Ser Ser
  1               5                  10                  15

Ile Ser Phe Leu Pro His Leu Glu Ala Lys Ile Arg Gln Thr His Asn
             20                  25                  30

Leu Ala Arg Leu Leu Thr Lys Tyr Ala Glu Gln Leu Leu Glu Glu Tyr
         35                  40                  45

Val Gln Gln Gln Gly Glu Pro Phe Gly Leu Pro Gly Phe Ser Pro Pro
     50                  55                  60

Arg Leu Pro Leu Ala Gly Leu Ser Gly Pro Ala Pro Ser His Ala Gly
 65                  70                  75                  80

Leu Pro Val Ser Glu Arg Leu Arg Gln Asp Ala Ala Ala Leu Ser Val
                 85                  90                  95

Leu Pro Ala Leu Leu Asp Ala Val Arg Arg Gln Ala Glu Leu Asn
            100                 105                 110

Pro Arg Ala Pro Arg Leu Leu Arg Ser Leu Glu Asp Ala Ala Arg Gln
        115                 120                 125

Val Arg Ala Leu Gly Ala Ala Val Glu Thr Val Leu Ala Ala Leu Gly
    130                 135                 140

Ala Ala Ala Arg Gly Pro Gly Pro Glu Pro Val Thr Val Ala Thr Leu
145                 150                 155                 160

Phe Thr Ala Asn Ser Thr Ala Gly Ile Phe Ser Ala Lys Val Leu Gly
                165                 170                 175

Phe His Val Cys Gly Leu Tyr Gly Glu Trp Val Ser Arg Thr Glu Gly
            180                 185                 190

Asp Leu Gly Gln Leu Val Pro Gly Gly Val Ala
        195                 200
```

<210> SEQ ID NO 9
<211> LENGTH: 200
<212> TYPE: PRT
<213> ORGANISM: primate

<400> SEQUENCE: 9

```
Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
     50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160
```

-continued

```
Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200


<210> SEQ ID NO 10
<211> LENGTH: 198
<212> TYPE: PRT
<213> ORGANISM: rodent

<400> SEQUENCE: 10

Met Ala Phe Ala Glu Gln Ser Pro Leu Thr Leu His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Met Glu Ser Tyr Val Lys His Gln Gly Leu Asn Lys Asn Ile
         35                  40                  45

Ser Leu Asp Ser Val Asp Gly Val Pro Val Ala Ser Thr Asp Arg Trp
     50                  55                  60

Ser Glu Met Thr Glu Ala Glu Arg Leu Gln Glu Asn Leu Gln Ala Tyr
 65                  70                  75                  80

Arg Thr Phe Gln Gly Met Leu Thr Lys Leu Leu Glu Asp Gln Arg Val
                 85                  90                  95

His Phe Thr Pro Thr Glu Gly Asp Phe His Gln Ala Ile His Thr Leu
            100                 105                 110

Thr Leu Gln Val Ser Ala Phe Ala Tyr Gln Leu Glu Glu Leu Met Ala
        115                 120                 125

Leu Leu Glu Gln Lys Val Pro Glu Lys Glu Ala Asp Gly Met Pro Val
    130                 135                 140

Thr Ile Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His His Met Gly Ile Ser Ala His Glu Ser His
            180                 185                 190

Tyr Gly Ala Lys Gln Met
        195


<210> SEQ ID NO 11
<211> LENGTH: 208
<212> TYPE: PRT
<213> ORGANISM: primate

<400> SEQUENCE: 11

Met Thr His Leu Ser Leu Leu Gly Pro Leu Pro Cys Val Arg Thr Ser
  1               5                  10                  15

Gln Gln Leu Pro Glu Thr Gln Gln Val Thr Thr Pro Gly Lys Lys Pro
             20                  25                  30

Val Ser Val Gly Arg Arg Glu Val Arg Val Pro Gly Thr Ala Leu Val
         35                  40                  45

Pro Ser Leu Leu Ser Val Ser Val Leu Leu Gln Leu Gln Tyr Gln Gly
     50                  55                  60

Ser Pro Phe Ser Asp Pro Gly Phe Ser Ala Pro Glu Leu Gln Leu Ser
 65                  70                  75                  80
```

-continued

```
Ser Leu Pro Pro Ala Thr Ala Phe Phe Lys Thr Trp His Ala Leu Asp
                85                  90                  95

Asp Gly Glu Arg Leu Ser Leu Ala Gln Arg Ala Ile Asp Pro His Leu
            100                 105                 110

Gln Leu Val Glu Asp Asp Gln Ser Asp Leu Asn Pro Gly Ser Pro Ile
        115                 120                 125

Leu Pro Ala Gln Leu Gly Ala Ala Arg Leu Arg Ala Gln Gly Pro Leu
    130                 135                 140

Gly Asn Met Ala Ala Ile Met Thr Ala Leu Gly Leu Pro Ile Pro Pro
145                 150                 155                 160

Glu Glu Asp Thr Pro Gly Leu Ala Ala Phe Gly Ala Ser Ala Phe Glu
                165                 170                 175

Arg Lys Cys Arg Gly Tyr Val Val Thr Arg Glu Tyr Gly His Trp Thr
            180                 185                 190

Asp Arg Ala Val Arg Asp Leu Ala Leu Leu Lys Ala Lys Tyr Ser Ala
        195                 200                 205


<210> SEQ ID NO 12
<211> LENGTH: 410
<212> TYPE: PRT
<213> ORGANISM: primate

<400> SEQUENCE: 12

Met Pro Ala Gly Arg Arg Gly Pro Ala Ala Gln Ser Ala Arg Arg Pro
  1               5                  10                  15

Pro Pro Leu Leu Pro Leu Leu Leu Leu Leu Cys Val Leu Gly Ala Pro
            20                  25                  30

Arg Ala Gly Ser Gly Ala His Thr Ala Val Ile Ser Pro Gln Asp Pro
        35                  40                  45

Thr Leu Leu Ile Gly Ser Ser Leu Leu Ala Thr Cys Ser Val His Gly
    50                  55                  60

Asp Pro Pro Gly Ala Thr Ala Glu Gly Leu Tyr Trp Thr Leu Asn Gly
 65                  70                  75                  80

Arg Arg Leu Pro Pro Glu Leu Ser Arg Val Leu Asn Ala Ser Thr Leu
                85                  90                  95

Ala Leu Ala Leu Ala Asn Leu Asn Gly Ser Arg Gln Arg Ser Gly Asp
            100                 105                 110

Asn Leu Val Cys His Ala Arg Asp Gly Ser Ile Leu Ala Gly Ser Cys
        115                 120                 125

Leu Tyr Val Gly Leu Pro Pro Glu Lys Pro Val Asn Ile Ser Cys Trp
    130                 135                 140

Ser Lys Asn Met Lys Asp Leu Thr Cys Arg Trp Thr Pro Gly Ala His
145                 150                 155                 160

Gly Glu Thr Phe Leu His Thr Asn Tyr Ser Leu Lys Tyr Lys Leu Arg
                165                 170                 175

Trp Tyr Gly Gln Asp Asn Thr Cys Glu Glu Tyr His Thr Val Gly Pro
            180                 185                 190

His Ser Cys His Ile Pro Lys Asp Leu Ala Leu Phe Thr Pro Tyr Glu
        195                 200                 205

Ile Trp Val Glu Ala Thr Asn Arg Leu Gly Ser Ala Arg Ser Asp Val
    210                 215                 220

Leu Thr Leu Asp Ile Leu Asp Val Val Thr Thr Asp Pro Pro Pro Asp
225                 230                 235                 240

Val His Val Ser Arg Val Gly Gly Leu Glu Asp Gln Leu Ser Val Arg
                245                 250                 255
```

-continued

Trp Val Ser Pro Pro Ala Leu Lys Asp Phe Leu Phe Gln Ala Lys Tyr
260 265 270

Gln Ile Arg Tyr Arg Val Glu Asp Ser Val Asp Trp Lys Val Val Asp
275 280 285

Asp Val Ser Asn Gln Thr Ser Cys Arg Leu Ala Gly Leu Lys Pro Gly
290 295 300

Thr Val Tyr Phe Val Gln Val Arg Cys Asn Pro Phe Gly Ile Tyr Gly
305 310 315 320

Ser Lys Lys Ala Gly Ile Trp Ser Glu Trp Ser His Pro Thr Ala Ala
325 330 335

Ser Thr Pro Arg Ser Glu Arg Pro Gly Pro Gly Gly Gly Ala Cys Glu
340 345 350

Pro Arg Gly Gly Glu Pro Ser Ser Gly Pro Val Arg Arg Glu Leu Lys
355 360 365

Gln Phe Leu Gly Trp Leu Lys Lys His Ala Tyr Cys Ser Asn Leu Ser
370 375 380

Phe Arg Leu Tyr Asp Gln Trp Arg Ala Trp Met Gln Lys Ser His Lys
385 390 395 400

Thr Arg Asn Gln Val Leu Pro Asp Lys Leu
405 410

<210> SEQ ID NO 13
<211> LENGTH: 407
<212> TYPE: PRT
<213> ORGANISM: rodent

<400> SEQUENCE: 13

Arg Pro Leu Ser Ser Leu Trp Ser Pro Leu Leu Leu Cys Val Leu Gly
1 5 10 15

Val Pro Arg Gly Gly Ser Gly Ala His Thr Ala Val Ile Ser Pro Gln
20 25 30

Asp Pro Thr Leu Leu Ile Gly Ser Ser Leu Gln Ala Thr Cys Ser Ile
35 40 45

His Gly Asp Thr Pro Gly Ala Thr Ala Glu Gly Leu Tyr Trp Thr Leu
50 55 60

Asn Gly Arg Arg Leu Pro Ser Leu Ser Arg Leu Leu Asn Thr Ser Thr
65 70 75 80

Leu Ala Leu Ala Leu Ala Asn Leu Asn Gly Ser Arg Gln Gln Ser Gly
85 90 95

Asp Asn Leu Val Cys His Ala Arg Asp Gly Ser Ile Leu Ala Gly Ser
100 105 110

Cys Leu Tyr Val Gly Leu Pro Pro Glu Lys Pro Phe Asn Ile Ser Cys
115 120 125

Trp Ser Arg Asn Met Lys Asp Leu Thr Cys Arg Trp Thr Pro Gly Ala
130 135 140

His Gly Glu Thr Phe Leu His Thr Asn Tyr Ser Leu Lys Tyr Lys Leu
145 150 155 160

Arg Trp Tyr Gly Gln Asp Asn Thr Cys Glu Glu Tyr His Thr Val Gly
165 170 175

Pro His Ser Cys His Ile Pro Lys Asp Leu Ala Leu Phe Thr Pro Tyr
180 185 190

Glu Ile Trp Val Glu Ala Thr Asn Arg Leu Gly Ser Ala Arg Ser Asp
195 200 205

Val Leu Thr Leu Asp Val Leu Asp Val Val Thr Thr Asp Pro Pro Pro

-continued

```
    210                 215                 220

Asp Val His Val Ser Arg Val Gly Gly Leu Glu Asp Gln Leu Ser Val
225                 230                 235                 240

Arg Trp Val Ser Pro Pro Ala Leu Lys Asp Phe Leu Phe Gln Ala Lys
                245                 250                 255

Tyr Gln Ile Arg Tyr Arg Val Glu Asp Ser Val Asp Trp Lys Val Val
            260                 265                 270

Asp Asp Val Ser Asn Gln Thr Ser Cys Arg Leu Ala Gly Leu Lys Pro
        275                 280                 285

Gly Thr Val Tyr Phe Val Gln Val Arg Cys Asn Pro Phe Gly Ile Tyr
    290                 295                 300

Gly Ser Lys Lys Ala Gly Ile Trp Ser Glu Trp Ser His Pro Thr Ala
305                 310                 315                 320

Ala Ser Thr Pro Arg Ser Glu Arg Pro Gly Pro Gly Gly Gly Val Cys
                325                 330                 335

Glu Pro Arg Gly Gly Glu Pro Ser Ser Gly Pro Val Arg Arg Glu Leu
            340                 345                 350

Lys Gln Phe Leu Gly Trp Leu Lys Lys His Ala Tyr Cys Ser Asn Leu
        355                 360                 365

Ser Phe Arg Leu Tyr Asp Gln Trp Arg Ala Trp Met Gln Lys Ser His
    370                 375                 380

Lys Thr Arg Asn Gln Asp Glu Gly Ile Leu Pro Ser Gly Arg Arg Gly
385                 390                 395                 400

Ala Ala Arg Gly Pro Ala Gly
                405
```